United States Patent
Truneh et al.

(10) Patent No.: US 9,932,402 B2
(45) Date of Patent: Apr. 3, 2018

(54) HUMANIZED ANTIBODIES TO INKT

(71) Applicant: NKT Therapeutics Inc., Waltham, MA (US)

(72) Inventors: Alemseged Truneh, Sudbury, MA (US); Francis Joseph Carr, Aberdeen (GB); Timothy David Jones, Cambridgeshire (GB); James P. Gregson, Cheshire (GB)

(73) Assignee: NKT Therapeutics Inc., Sharon, MA (US)

( * ) Notice: Subject to any disclaimer, the term of this patent is extended or adjusted under 35 U.S.C. 154(b) by 0 days.

(21) Appl. No.: 13/661,386

(22) Filed: Oct. 26, 2012

(65) Prior Publication Data

US 2013/0136735 A1     May 30, 2013

Related U.S. Application Data

(60) Provisional application No. 61/552,337, filed on Oct. 27, 2011.

(51) Int. Cl.
*A61K 39/395* (2006.01)
*C07K 16/28* (2006.01)
*A61K 39/00* (2006.01)

(52) U.S. Cl.
CPC .... *C07K 16/2809* (2013.01); *A61K 2039/505* (2013.01); *A61K 2039/543* (2013.01); *C07K 2317/24* (2013.01); *C07K 2317/41* (2013.01); *C07K 2317/56* (2013.01); *C07K 2317/71* (2013.01); *C07K 2317/72* (2013.01); *C07K 2317/73* (2013.01); *C07K 2317/732* (2013.01); *C07K 2317/734* (2013.01); *C07K 2317/75* (2013.01); *C07K 2317/76* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 7,101,977 B2 | 9/2006 | Rosenblum et al. | |
| 7,666,411 B2 | 2/2010 | Strober et al. | |
| 7,682,614 B2* | 3/2010 | Strober et al. | 424/144.1 |
| 8,012,484 B2 | 9/2011 | Linden et al. | |
| 8,138,314 B2 | 3/2012 | Exley et al. | |
| 8,173,123 B2 | 5/2012 | Strober et al. | |
| 8,821,866 B2 | 9/2014 | Strober et al. | |
| 2002/0164331 A1 | 11/2002 | Exley et al. | |
| 2006/0052316 A1 | 3/2006 | Porcelli | |
| 2006/0116332 A1* | 6/2006 | Strober et al. | 514/25 |
| 2006/0269540 A1 | 11/2006 | Robert et al. | |
| 2007/0160600 A1 | 7/2007 | Exley et al. | |
| 2008/0254037 A1 | 10/2008 | Linden et al. | |
| 2009/0028849 A1 | 1/2009 | O'Brien et al. | |
| 2010/0035843 A1 | 2/2010 | Wilson et al. | |
| 2010/0197613 A1* | 8/2010 | Strober et al. | 514/25 |
| 2012/0258040 A1 | 10/2012 | Exley et al. | |
| 2013/0039886 A1 | 2/2013 | Berzofsky et al. | |
| 2014/0301996 A1 | 10/2014 | Umetsu et al. | |
| 2015/0165021 A1 | 6/2015 | Mashal et al. | |
| 2016/0022777 A1 | 1/2016 | Schaub et al. | |

FOREIGN PATENT DOCUMENTS

| | | |
|---|---|---|
| EP | 0677533 A2 | 10/1995 |
| WO | WO 1997/016203 A1 | 5/1997 |
| WO | WO 1999/034209 A1 | 7/1999 |
| WO | WO 2001/098357 A2 | 12/2001 |
| WO | WO 2007/027713 A2 | 3/2007 |
| WO | WO 2008/140487 A2 | 11/2008 |
| WO | WO 2009/026412 A1 | 2/2009 |
| WO | WO 2009/070648 A2 | 6/2009 |
| WO | WO 2010/094981 A1 | 8/2010 |
| WO | WO 2013/079687 A1 | 6/2013 |

OTHER PUBLICATIONS

Mariuzza, R.A. et al. 'The Structural Basis of Antigen-Antibody Recognition' Annu. Rev. Biophys. Biphys. Chem. 16:139-159, 1987.*
Rudikoff et al. "Single Amino Acid Substitution Altering Antigen-Binding Specificity" PNAS. 79:1979-1983, 1982.*
Rader et al. PNAS. 95:8910-8915, 1998.*
Berzins et al. 'Natural killer T cells: drivers or passengers in preventing human disease?' Nature Rev. 14:640-646, 2014.*
Scheuplein et al. 'A Humanized Monoclonal Antibody Specific for Invariant Natural Killer T (iNKT) Cells for In Vivo Depletion.' PLOS ONE 8(9): e76692. doi:10.1371/journal.pone.0076692.*
Das et al. 'Cancer immunotherapeutic potential of NKTT320, a novel human invariant natural killer T-cell activating monoclonal antibody.' Cancer Research 75:4294, 2015.*
International Search Report and Written Opinion dated Jan. 28, 2013 for PCT/US2012/062124.
International Preliminary Report on Patentability dated May 8, 2014 for PCT/US2012/062124.
Australian Office Action dated Jun. 20, 2014 for Application No. AU 2012328588.
Canadian Office Action dated Jul. 11, 2014 for Application No. CA 2,853,719.
European Search Report dated Jul. 9, 2014 for Application No. EP 12843689.6.
European Office Action dated Jul. 25, 2014 for Application No. EP 12843689.6.

(Continued)

*Primary Examiner* — Nora Rooney
(74) *Attorney, Agent, or Firm* — Wolf, Greenfield & Sacks, P.C.

(57) ABSTRACT

Methods of treatment to suppress an immune response are provided. The method comprises administering to a subject in need of treatment a naked blocking antibody that binds selectively iNKT cells in an amount effective to suppress the subject's iNKT cell function. Compositions comprising, an isolated, humanized antibody that binds selectively iNKT cells are also provided.

7 Claims, 11 Drawing Sheets

(56) References Cited

OTHER PUBLICATIONS

Behar et al., Diverse TCRs recognize murine CD1. J Immunol. Jan. 1, 1999; 162(1):161-7.
Bendelac et al., Mouse CD1-specific NK1 T cells: development, specificity, and function. Annu Rev Immunol. 1997; 15:535-562.
Bendelac et al., The biology of NKT cells. Annu Rev Immunol. 2007; 25:297-336.
Busse et al., Safety profile, pharmacokinetics, and biologic activity of MEDI-563, an anti-IL-5 receptor alpha antibody, in a phase I study of subjects with mild asthma. J Allergy Clin Immunol. 2010; 125:1237-1244 e1232.
Campbell, Monoclonal Antibody Technology, Elsevier Science Publishers B.V., 1985; 2$^{nd}$ Edition, Chapter 1:1-32.
Dellabona et al., An invariant Valpha24-JalphaQ/Vbeta11 T cell receptor is expressed in all individuals by clonally expanded CD4-8- T cells. J Exp Med. Sep. 1, 1994; 180(3):1171-6.
Exley et al., Requirement of CD1d recognition by human invariant Valpha24+ CD4-CD8- T cells. J Exp Med. 1997; 186:109-120.
Exley et al., Isolation and functional use of human NKT cells. Current Protocols in Immunology 2002; 14.11.1-14.11.13.
Exley et al., Selective activation, expansion, and monitoring of human iNKT cells with a monoclonal antibody specific for the TCE alpha-chain CDR3 loop. Eur J Immunol. 2008; 38:1756-1766.
Field et al., Targeting iNKT cells for the treatment of sickle cell disease. Clinical Immunology. Mar. 2, 2011; 140(2):177-183.
Garcia et al., Structural basis of T cell recognition. Annu Rev Immunol. 1999; 17:369-397.
Gavilondo et al., Antibody engineering at the millennium. Biotechniques. 2000; 29:128-145.
Harlow et al. Antibodies A Laboratory Manual, Cold Spring Harbor Press, 1988; pp. content vi, Chapter 9:321-358.
Jameson et al., The T cell receptor V alpha11 gene family.The Journal of Immunology. 1991; 147:3185-3193.
Janeway et al., Immunobiology, Current Biology Limited. 3$^{rd}$ Edition. 1997; p. 4:36.
Janeway et al., Immunobiology, 5$^{th}$ Edition, Garland Science. 2001; 94-105.
Junttila et al. Superior in vivo efficacy of afucosylated trastuzumab in the treatment of HER2-amplified breast cancer. Cancer Res. 2010; 70:4481-4489.
Kent et al., Noncanonical Valpha24JalphaQ T cells with conservative alpha china CDR3 region amino acid substitutions are restricted by CD1. Human Immunology. 1999; 60:1080-1089.
Kim et al. Persistent activation of an innate immune response translates respiratory viral infection into chronic lung disease. Nat Med. 2008; 14:633-640.
Kuhnlein et al., Identification and characterization of Rat gamma/delta T lymphocytes in peripheral lymphoid organs, small intestine, and skin with a monoclonal antibody to a constant determinant of the gamma/delta T cell receptor. J Immunol. Aug. 1, 1994; 153(3):979-86.
Kuns et al. Invariant natural killer T cell-natural killer cell interactions dictate transplantation outcome after alpha-galactosylceramide administration. Blood. 2009; 113:5999-6010.
Laune et al., Clinical Chemistry and Laboratory Medicine. 1998; 36(6):367-371.
Lehuen et al. Immune cell crosstalk in type 1 diabetes. Nat Rev Immunol. 2010; 10:501-513.
Lisbonne et al. Cutting edge: invariant V alpha 14 NKT cells are required for allergen-induced airway inflammation and hyper-reactivity in an experimental asthma model. J Immunol. 2003; 171:1637-1641.
Lombardi et al. A CD1d-dependent antagonist inhibits the activation of invariant NKT cells and prevents development of allergen-induced airway hyperreactivity. J Immunol. 2010; 184:2107-2115.
Matangkasombut et al. Direct activation of natural killer T cells induces airway hyperreactivity in nonhuman primates. J Allergy Clin Immunol. 2008; 121:1287-1289.
Matangkasombut et al. Natural killer T cells in the lungs of patients with asthma. J Allergy Clin Immunol. 2009 123:1181-1185.
Matangkasombut et al. Natural killer T cells and the regulation of asthma. Mucosal Immunology. Sep. 1, 2009; 2(5):383-392.
Matsuda et al. CD1d-restricted iNKT cells, the 'Swiss-Army knife' of the immune system. Curr Opin Immunol. 2008; 20:358-368.
Meyer et al. Glycolipid activation of invariant T cell receptor+ NK T cells is sufficient to induce airway hyperreactivity independent of conventional CD4+ T cells. Proc Natl Acad Sci U S A. 2006; 103:2782-2787.
Newman et al., Modification of the Fc region of a primatized IgG antibody to human CD4 retains its ability to modulate CD4 receptors but does not deplete CD4+ T cells in chimpanzees. Clin Immunol. 2001; 98:164-174.
Niwa et al. Defucosylated chimeric anti-CC chemokine receptor 4 IgG1 with enhanced antibody-dependent cellular cytotoxicity shows potent therapeutic activity to T-cell leukemia and lymphoma. Cancer Res. 2004; 64:2127-2133.
Oishi et al., CD4-CD8- T cells bearing invariant Valpha24JalphaQ TCR alpha-chain are decreased in patients with atopic diseases. Clin Exp Immunol. 2000; 119:404-411.
Pichavant et al. Ozone exposure in a mouse model induces airway hyperreactivity that requires the presence of natural killer T cells and IL-17. J Exp Med. 2008; 205:385-393. Supplemental Material included.
Prussin et al., TCR Va24 and Vbeta11 coexpression defines a human NK1 T cell analog containing a unique Th0 subpopulation. J Immunol. 1997; 159:5862-5870.
Reddy et al., Elimination of Fc receptor-dependent effector functions of a modified IgG4 monoclonal antibody to human CD4. The Journal of Immunology. 2000; 1925-1933.
Reynolds et al. Natural killer T cells in bronchial biopsies from human allergen challenge model of allergic asthma. J Allergy Clin Immunol. 2009; 124:860-862; author reply 862.
Satoh et al., Cytotoxic gammadelta or alphabeta T cells with a natural killer cell marker, CD56, induced from human peripheral blood lymphocytes by a combination of IL-12 and IL-2. J Immunol. Nov. 1, 1996; 157(9):3886-92.
Scheuplein et al. A humanized monoclonal antibody specific for invariant natural killer T (iNKT) cells for in vivo depletion. PLOS One. Sep. 1, 2013; 8(9):e76692.
Scichilone et al., Clinical implications of airway hyper-responsiveness in COPD. International Journal of COPD. 2006; 1(1):46-60. Article retrieved from the Internet on Jan. 9, 2013.
Shinkawa et al. The absence of fucose but not the presence of galactose or bisecting N-acetylglucosamine of human IgG1 complex-type oligosaccharides shows the critical role of enhancing antibody-dependent cellular cytotoxicity. J Biol Chem. 2003; 278:3466-3473.
Sido et al., Differential immunosuppressive activity of monoclonal CD2 antibodies on allograft rejection versus specific antibody production. Eur J Immunol. 1998; 28:1347-1357.
Smiley et al., Immunoglobulin E production in the absence of interleukin-4-secreting CD1-dependent cells. Science. Feb. 14, 1997; 275(5302):977-9.
Sonoda et al., CD1-reactive natural killer T cells are required for development of systemic tolerance through an immune-privileged site. J Exp Med. Nov. 1, 1999; 190(9):1215-26.
Tojo et al. A chromatographic approach for elevating the antibody-dependent cellular cytotoxicity of antibody composites. Biol Pharm Bull. 2009; 32:1604-1608.
Umetsu et al. Natural killer T cells are important in the pathogenesis of asthma: the many pathways to asthma. J Allergy Clin Immunol. 2010; 125:975-979.
Van Kaer et al. Invariant natural killer T cells: bridging innate and adaptive immunity. Cell Tissue Res. 2011; 343:43-55.
Van Kaer. NKT cells: T lymphocytes with innate effector functions. Curr Opin Immunol. 2007; 19:354-364.
Younes et al., Phase II clinical trial of interleukin-12 in patients with relapsed and refractory non-Hodgkin's lymphoma and Hodgkin's disease. Clin Cancer Res. Aug. 15, 2004;10(16):5432-8.
Zhu et al., The Pro-Th1 cytokine IL-12 enhances IL-4 production by invariant NKT cells: relevance for T cell-mediated hepatitis. J Immunol. May 1, 2007;178(9):5435-42.

(56) References Cited

OTHER PUBLICATIONS

Ishida et al., [The expression technology of chimeric and humanized antibodies]. Nihon Rinsho. Mar. 2002;60(3):439-44.
Nakamura et al., CD4+ NKT cells, but not conventional CD4+ T cells, are required to generate efferent CD8+ T regulatory cells following antigen inoculation in an immune-privileged site. J Immunol. Aug. 1, 2003;171(3):1266-71.
Patterson et al., Human invariant NKT cells are required for effective in vitro alloresponses. J Immunol. Oct. 15, 2005;175(8):5087-94.
Saito et al., Invariant NKT cells are required for antitumor responses induced by host-versus-graft responses. J Immunol. Aug. 15, 2010;185(4):2099-105. doi: 10.4049/jimmunol.0901985. Epub Jul. 14, 2010.
U.S. Appl. No. 14/810,587, filed Jul. 28, 2015, Schaub et al.
PCT/US2015/042352, Oct. 28, 2015, International Search Report and Written Opinion.
International Search Report and Written Opinion dated Oct. 28, 2015 for PCT/US2015/042352.
Cammack et al., IC50. In: Oxford Dictionary of Biochemistry and Molecular Biology. 2000. Oxford University Press, revised ed., p. 322.
Corgnac et al., CD1d-antibody fusion proteins target iNKT cells to the tumor and trigger long-term therapeutic responses. Cancer Immunol Immunother. Apr. 2013;62(4):747-60. doi: 10.1007/s00262-012-1381-7.
Lo, Antibody humanization by CDR grafting. Methods Mol Biol. 2004;248:135-59.
Lu, Structure and function of CD1d molecules. Chemistry of Life. 2008;28(2):159-161.
Nakui et al., Potentiation of antitumor effect of NKT cell ligand, alpha-galactosylceramide by combination with IL-12 on lung metastasis of malignant melanoma cells. Clin Exp Metastasis. 2000;18(2):147-53.
Terabe et al., The role of NKT cells in tumor immunity. Adv Cancer Res. 2008;101:277-348. doi: 10.1016/S0065-230X(08)00408-9.
Tyznik et al., Distinct requirements for activation of NKT and NK cells during viral infection. J Immunol. Apr. 15, 2014;192(8):3676-85. doi: 10.4049/jimmunol.1300837. Epub Mar. 14, 2014.
Yarilin, Fundamentals of Immunology. Moscow: Meditsina Publishers; 1999. p. 178, Table 40 on p. 182; pp. 147-148.

\* cited by examiner

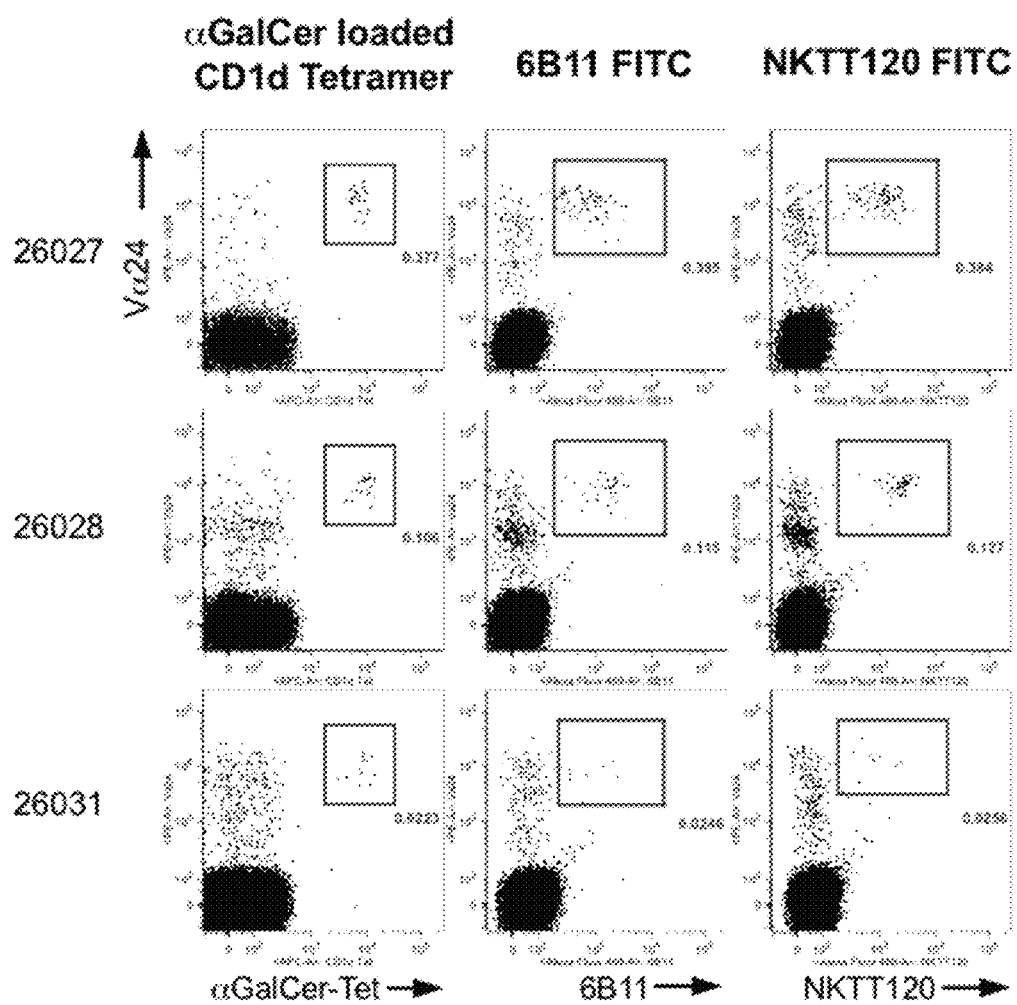
Figure :1 NKTT120 Binding to Human Peripheral Blood iNKT Cells

Figure 2: Blocking of CD1d-tetramer Binding to iNKT Cells by NKTT120
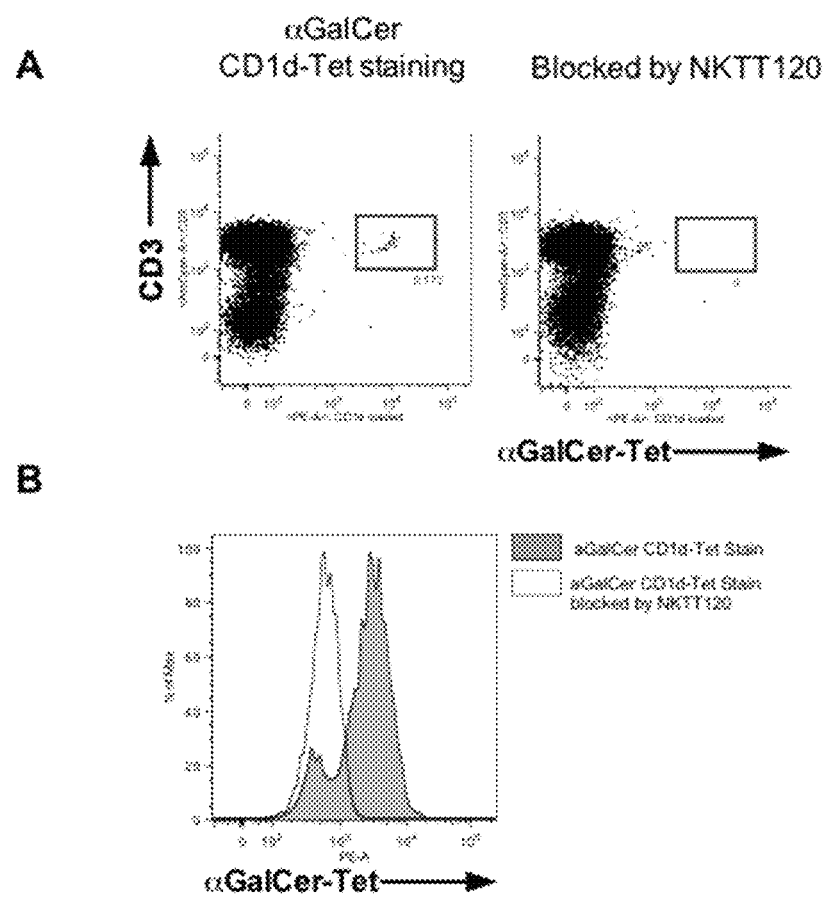

Figure 3: Depletion of iNKT Cells in Blood Spleen and Lymph Node by NKTT120
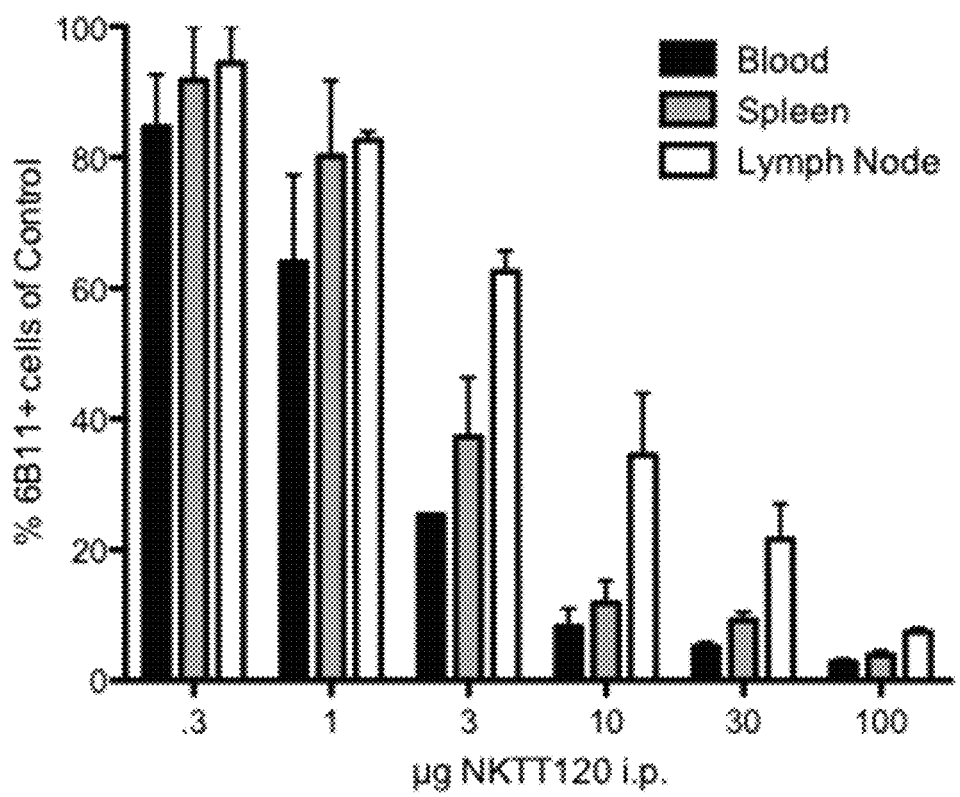

Figure 4: Time Course of iNKT Cell Depletion by NKTT120 in Vα24 Transgenic Mice
A
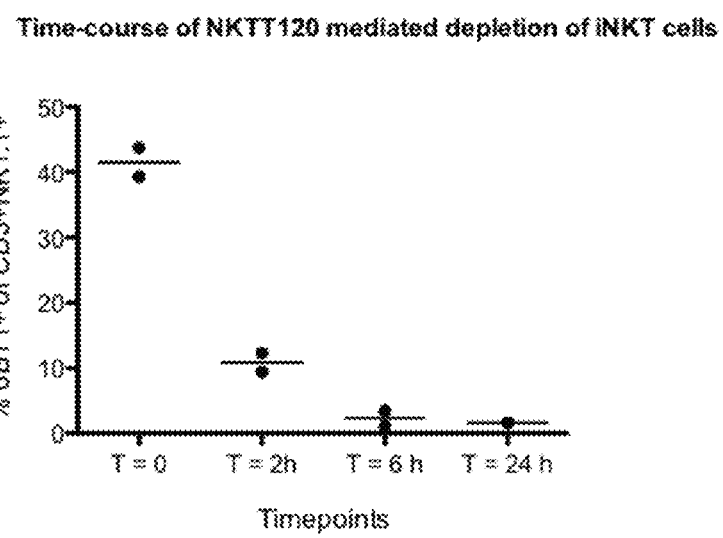
B
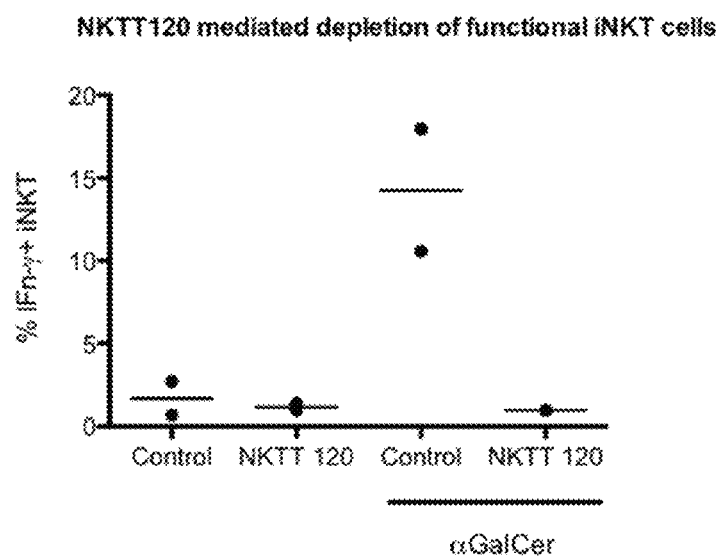

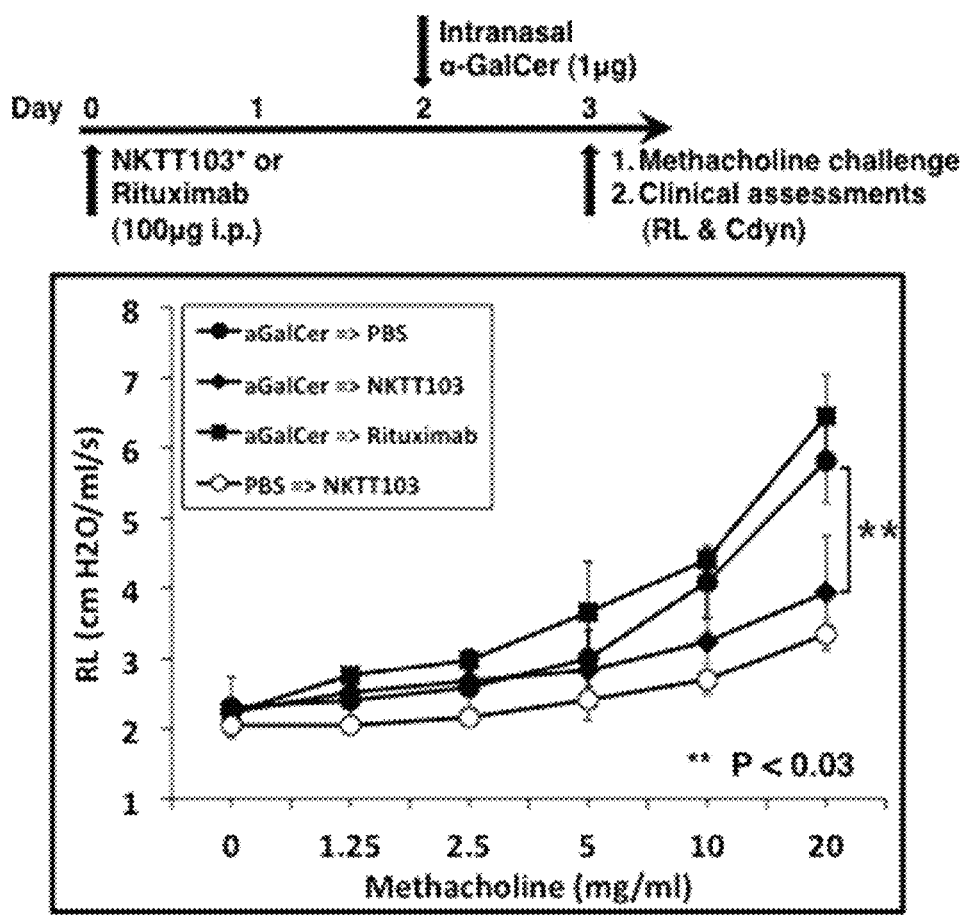
Figure 5: Pharmacologic Depletion of iNKT Cells in Vα24 Transgenic Mice Abrogates α-GalCer-Mediated iNKT Cell-dependent AHR

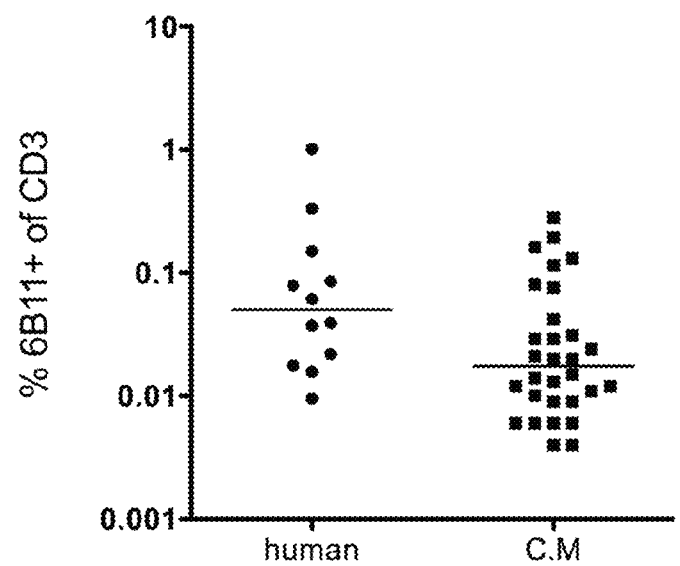
Figure 6: Comparison of Human and Cynomolgus Monkey iNKT Cell Frequencies Figure 7: Comparison of Saturation binding to Human and Cynomolgus Monkey iNKT Cells.
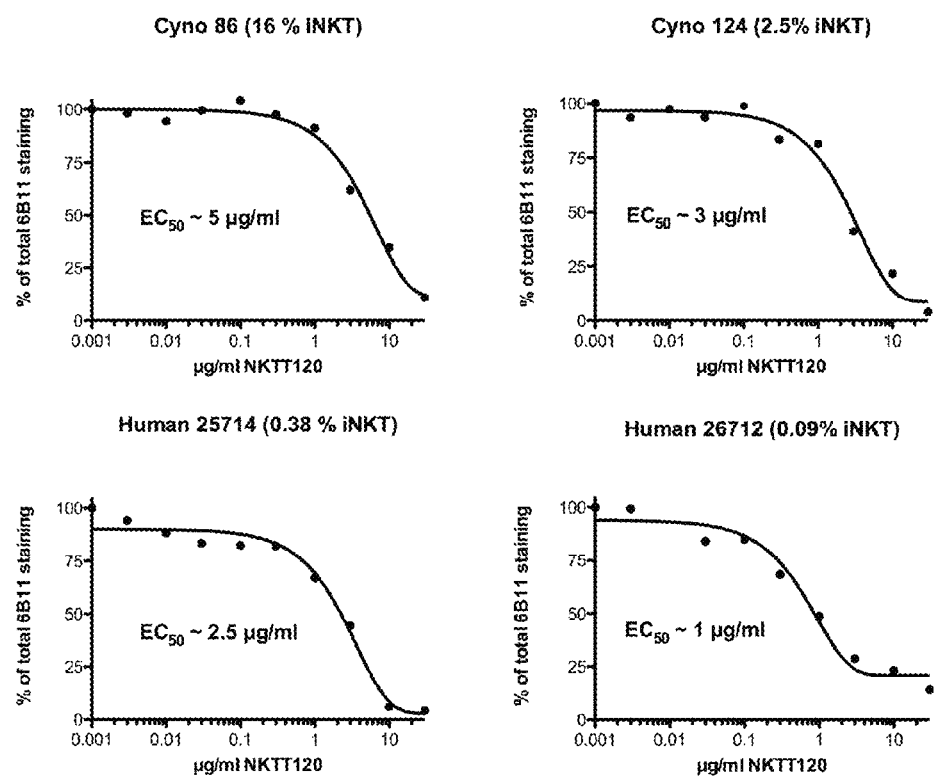

Figure 8: iNKT Cell Depletion by NKTT120 24 Hours After Dosing
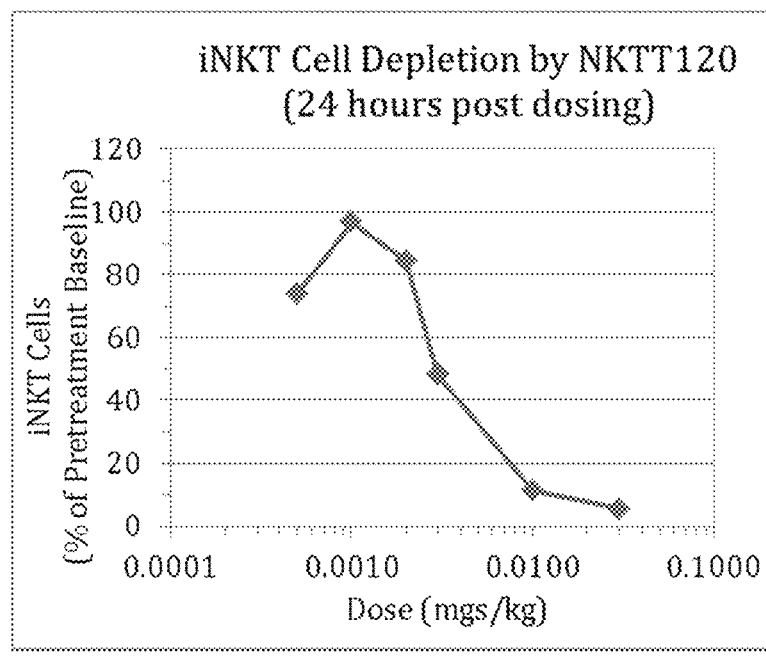

Figure 9: iNKT Cell Depletion by NKTT120 in Cynomolgus Monkeys
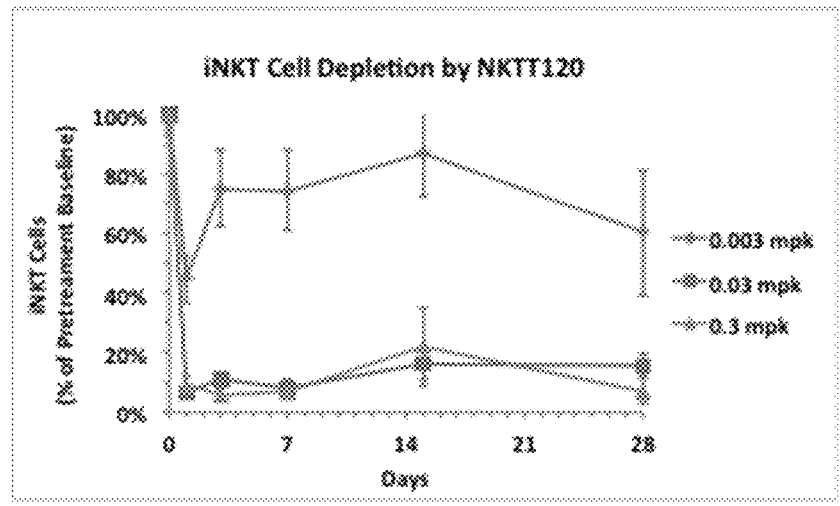
NKTT120 dose response of the depletion of iNKT cells in cynomolgus monkeys.
Figure 10: Effect of NKTT120 on iNKT, B and T Cells
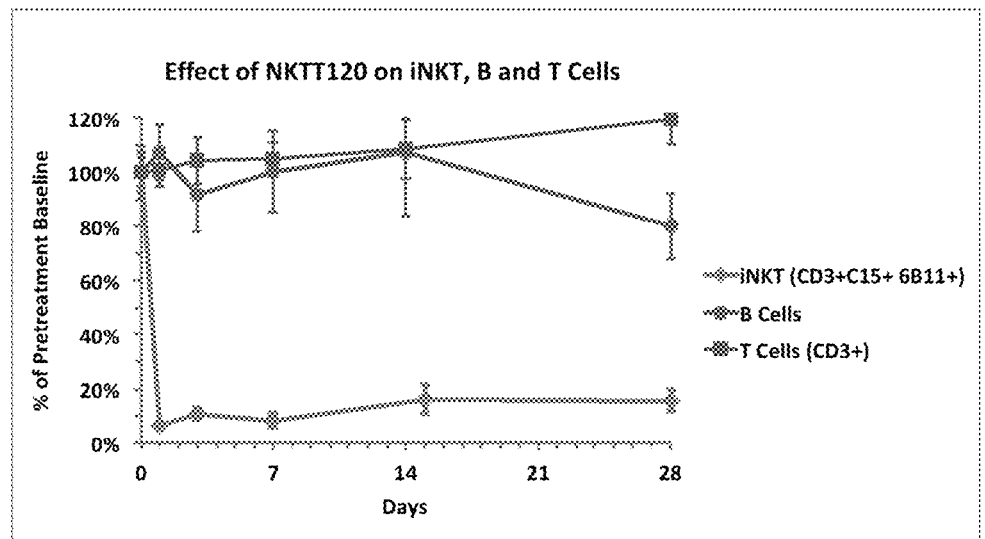
NKTT120 (0.03 mg/kg) treatment has no significant effect on B cells and other T cells.

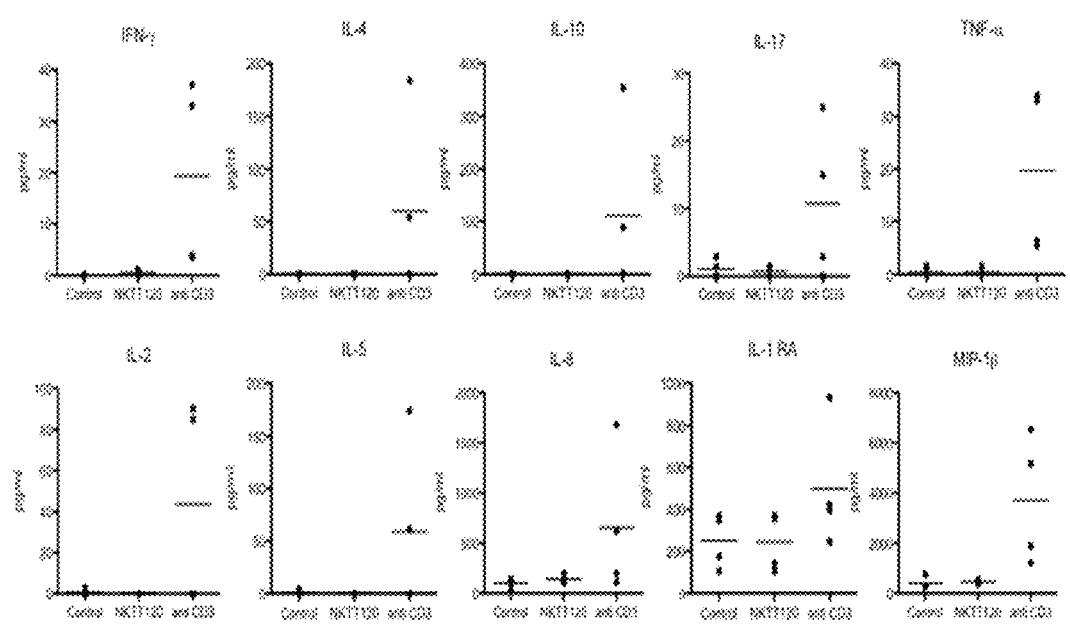
Figure 11: Effect of NKTT120 Cytokine Levels in Human Whole Blood

SEQUENCE LISTING

```
<160> NUMBER OF SEQ ID NOS: 31

<210> SEQ ID NO 1
<211> LENGTH: 14
<212> TYPE: PRT
<213> ORGANISM: Homo sapiens

<400> SEQUENCE: 1

Cys Val Val Ser Asp Arg Gly Ser Thr Leu Gly Arg Leu Tyr
1               5                   10

<210> SEQ ID NO 2
<211> LENGTH: 14
<212> TYPE: PRT
<213> ORGANISM: Macaca fascicularis
```

<400> SEQUENCE: 2

Cys Val Val Ser Asp Arg Gly Ser Thr Leu Gly Lys Leu Tyr
1               5                   10

<210> SEQ ID NO 3
<211> LENGTH: 14
<212> TYPE: PRT
<213> ORGANISM: Macaca mulatta

<400> SEQUENCE: 3

Cys Val Val Ser Asp Arg Gly Ser Thr Leu Gly Lys Leu Tyr
1               5                   10

<210> SEQ ID NO 4
<211> LENGTH: 14
<212> TYPE: PRT
<213> ORGANISM: Mus musculus

<400> SEQUENCE: 4

Cys Val Val Gly Asp Arg Gly Ser Ala Leu Gly Arg Leu His
1               5                   10

<210> SEQ ID NO 5
<211> LENGTH: 14
<212> TYPE: PRT
<213> ORGANISM: Rattus rattus

<400> SEQUENCE: 5

Cys Val Val Ala Asp Arg Gly Ser Ala Leu Gly Lys Leu Tyr
1               5                   10

<210> SEQ ID NO 6
<211> LENGTH: 14
<212> TYPE: PRT
<213> ORGANISM: Sus scrofa domestica

<400> SEQUENCE: 6

Cys Val Val Gly Asp Arg Gly Ser Arg Leu Gly Arg Leu Tyr
1               5                   10

<210> SEQ ID NO 7
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 7

Glu Val Lys Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95

Tyr Cys Thr Arg Asn Gly Asn Tyr Val Asp Tyr Ala Met Asp Tyr Trp

-continued

```
                100                 105                 110
Gly Gln Gly Thr Ser Val Thr Val Ser Ser
        115                 120

<210> SEQ ID NO 8
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 8

Glu Val Lys Leu Val Glu Ser Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95

Tyr Cys Thr Arg Asn Gly Asn Tyr Val Asp Tyr Ala Met Asp Tyr Trp
            100                 105                 110

Gly Gln Gly Thr Leu Val Thr Val Ser Ser
        115                 120

<210> SEQ ID NO 9
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Gly Val Tyr
                85                  90                  95

Tyr Cys Thr Arg Asn Gly Asn Tyr Val Asp Tyr Ala Met Asp Tyr Trp
            100                 105                 110

Gly Gln Gly Thr Leu Val Thr Val Ser Ser
        115                 120

<210> SEQ ID NO 10
<211> LENGTH: 122
<212> TYPE: PRT
<213> ORGANISM: Artificial sequence
<220> FEATURE:
```

<223> OTHER INFORMATION: NKTT antibody heavy chain sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Arg Asn Gly Asn Tyr Val Asp Tyr Ala Met Asp Tyr Trp
            100                 105                 110

Gly Gln Gly Thr Leu Val Thr Val Ser Ser
        115                 120

<210> SEQ ID NO 11
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Arg Asn Gly Asn Tyr Val Asp Tyr Ala Met Asp Tyr Trp
            100                 105                 110

Gly Gln Gly Thr Leu Val Thr Val Ser Ser
        115                 120

<210> SEQ ID NO 12
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 12

Glu Val Lys Leu Gln Glu Ser Gly Pro Gly Leu Val Lys Pro Pro Gly
1               5                   10                  15

Thr Met Ser Leu Thr Cys Val Ala Ser Gly Phe Thr Phe Ser Asn Tyr
            20                  25                  30

Trp Met Asn Trp Val Arg Gln Pro Pro Gly Lys Gly Leu Glu Trp Val

```
                35                  40                  45
Ala Glu Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Ser Gln
65                  70                  75                  80

Val Ser Leu Lys Met Ser Ser Val Thr Ala Val Asp Thr Gly Val Tyr
                85                  90                  95

Tyr Cys Thr Arg Asn Gly Asn Tyr Val Asp Tyr Ala Met Asp Tyr Trp
                100                 105                 110

Gly Gln Gly Thr Leu Val Thr Val Ser Ser
        115                 120

<210> SEQ ID NO 13
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 13

Glu Val Lys Leu Val Glu Ser Gly Ala Glu Val Lys Lys Pro Gly Ala
1               5                   10                  15

Ser Met Lys Leu Ser Cys Val Ala Ser Gly Phe Thr Phe Ser Asn Tyr
                20                  25                  30

Trp Met Asn Trp Val Arg Gln Ala Pro Gly Lys Gly Leu Glu Trp Val
            35                  40                  45

Ala Glu Ile Arg Leu Lys Ser Asn Asn Tyr Ala Thr His Tyr Ala Glu
        50                  55                  60

Ser Val Lys Gly Arg Phe Thr Ile Thr Arg Asp Asp Ser Thr Ser Thr
65                  70                  75                  80

Val Tyr Leu Glu Met Ser Ser Leu Arg Ser Glu Asp Thr Gly Val Tyr
                85                  90                  95

Tyr Cys Thr Arg Asn Gly Asn Tyr Val Asp Tyr Ala Met Asp Tyr Trp
                100                 105                 110

Gly Gln Gly Thr Leu Val Thr Val Ser Ser
        115                 120

<210> SEQ ID NO 14
<211> LENGTH: 122
<212> TYPE: PRT
<213> ORGANISM: Artificial sequence
<220> FEATURE:
<223> OTHER INFORMATION: NKTT antibody heavy chain sequence

<400> SEQUENCE: 14

Glu Val Lys Leu Lys Glu Ser Gly Pro Ala Leu Val Lys Pro Thr Gln
1               5                   10                  15

Thr Met Thr Leu Thr Cys Val Ala Ser Gly Phe Thr Phe Ser Asn Tyr
                20                  25                  30

Trp Met Asn Trp Val Arg Gln Pro Pro Gly Lys Ala Leu Glu Trp Val
            35                  40                  45

Ala Glu Ile Arg Leu Lys Ser Asn Asn Tyr Ala Thr His Tyr Ala Glu
        50                  55                  60

Ser Val Lys Gly Arg Phe Thr Ile Ser Arg Asp Asp Ser Lys Ser Gln
65                  70                  75                  80

Val Val Leu Thr Met Thr Asn Met Asp Pro Val Asp Thr Gly Thr Tyr
                85                  90                  95
```

```
Tyr Cys Thr Arg Asn Gly Asn Tyr Val Asp Tyr Ala Met Asp Tyr Trp
                100                 105                 110
Gly Gln Gly Thr Leu Val Thr Val Ser Ser
        115                 120

<210> SEQ ID NO 15
<211> LENGTH: 107
<212> TYPE: PRT
<213> ORGANISM: Artificial sequence
<220> FEATURE:
<223> OTHER INFORMATION: NKTT antibody light chain sequence

<400> SEQUENCE: 15

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Phe Ala Leu Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 16
<211> LENGTH: 107
<212> TYPE: PRT
<213> ORGANISM: Artificial sequence
<220> FEATURE:
<223> OTHER INFORMATION: NKTT antibody light chain sequence

<400> SEQUENCE: 16

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 17
<211> LENGTH: 107
<212> TYPE: PRT
<213> ORGANISM: Artificial sequence
<220> FEATURE:
<223> OTHER INFORMATION: NKTT antibody light chain sequence

<400> SEQUENCE: 17

Asp Ile Val Met Thr Gln Ser Pro Ser Ser Leu Ser Ala Ser Val Gly
```

```
1               5                   10                  15
Asp Arg Val Thr Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Tyr Cys Gln Gln His Tyr Ser Thr Pro Trp
                85                  90                  95

Thr Phe Gly Gln Gly Thr Lys Leu Glu Ile Lys
                100                 105

<210> SEQ ID NO 18
<211> LENGTH: 107
<212> TYPE: PRT
<213> ORGANISM: Artificial sequence
<220> FEATURE:
<223> OTHER INFORMATION: NKTT antibody light chain sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Tyr Cys Gln Gln His Tyr Ser Thr Pro Trp
                85                  90                  95

Thr Phe Gly Gln Gly Thr Lys Leu Glu Ile Lys
                100                 105

<210> SEQ ID NO 19
<211> LENGTH: 107
<212> TYPE: PRT
<213> ORGANISM: Artificial sequence
<220> FEATURE:
<223> OTHER INFORMATION: NKTT antibody light chain sequence

<400> SEQUENCE: 19

Asp Ile Val Met Thr Gln Ser Pro Ala Thr Leu Ser Val Ser Pro Gly
1               5                   10                  15

Glu Arg Ala Thr Leu Ser Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Ile Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Phe Ala Leu Tyr Tyr Cys Gln Gln His Tyr Ser Thr Pro Trp
                85                  90                  95
```

```
Thr Phe Gly Gln Gly Thr Lys Leu Glu Ile Lys
            100                 105
```

```
<210> SEQ ID NO 20
<211> LENGTH: 107
<212> TYPE: PRT
<213> ORGANISM: Artificial sequence
<220> FEATURE:
<223> OTHER INFORMATION: NKTT antibody light chain sequence

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Asp Val Ser Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Lys Ile Ser Arg Val Glu Ala
65                  70                  75                  80

Glu Asp Val Gly Leu Tyr Tyr Cys Gln Gln His Tyr Ser Thr Pro Trp
                85                  90                  95

Thr Phe Gly Gln Gly Thr Lys Leu Glu Ile Lys
            100                 105
```

```
<210> SEQ ID NO 21
<211> LENGTH: 5
<212> TYPE: PRT
<213> ORGANISM: Artificial sequence
<220> FEATURE:
<223> OTHER INFORMATION: CDR H1

<400> SEQUENCE: 21

Asn Tyr Trp Met Asn
1               5
```

```
<210> SEQ ID NO 22
<211> LENGTH: 21
<212> TYPE: PRT
<213> ORGANISM: Artificial sequence
<220> FEATURE:
<223> OTHER INFORMATION: CDR H2

<400> SEQUENCE: 22

Val Ala Glu Ile Arg Leu Lys Ser Asn Asn Tyr Ala Thr His Tyr Ala
1               5                   10                  15

Glu Ser Val Lys Gly
            20
```

```
<210> SEQ ID NO 23
<211> LENGTH: 11
<212> TYPE: PRT
<213> ORGANISM: Artificial sequence
<220> FEATURE:
<223> OTHER INFORMATION: CDR H3

<400> SEQUENCE: 23

Asn Gly Asn Tyr Val Asp Tyr Ala Met Asp Tyr
1               5                   10
```

```
<210> SEQ ID NO 24
<211> LENGTH: 11
```

-continued

```
<212> TYPE: PRT
<213> ORGANISM: Artificial sequence
<220> FEATURE:
<223> OTHER INFORMATION: CDR V1

<400> SEQUENCE: 24

Lys Ala Ser Gln Asp Val Ser Thr Ala Val Ala
1               5                   10

<210> SEQ ID NO 25
<211> LENGTH: 7
<212> TYPE: PRT
<213> ORGANISM: Artificial sequence
<220> FEATURE:
<223> OTHER INFORMATION: CDR V2

<400> SEQUENCE: 25

Trp Ala Ser Thr Arg His Thr
1               5

<210> SEQ ID NO 26
<211> LENGTH: 9
<212> TYPE: PRT
<213> ORGANISM: Artificial sequence
<220> FEATURE:
<223> OTHER INFORMATION: CDR V3

<400> SEQUENCE: 26

Gln Gln His Tyr Ser Thr Pro Trp Thr
1               5

<210> SEQ ID NO 27
<211> LENGTH: 452
<212> TYPE: PRT
<213> ORGANISM: Artificial sequence
<220> FEATURE:
<223> OTHER INFORMATION: NKTT120 Heavy chain sequence (Translation of
      VH4-G1)

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Arg Asn Gly Asn Tyr Val Asp Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Val Val Thr
            180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 28
<211> LENGTH: 449
<212> TYPE: PRT
<213> ORGANISM: Artificial sequence
<220> FEATURE:
<223> OTHER INFORMATION: NKTT320 Heavy chain sequence (Translation of
      VH4-G4)

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Thr
```

```
            65                  70                  75                  80
        Val Tyr Leu Gln Met Asn Ser Leu Arg Ala Glu Asp Thr Ala Val Tyr
                        85                  90                  95

Tyr Cys Thr Arg Asn Gly Asn Tyr Val Asp Tyr Ala Met Asp Tyr Trp
                       100                 105                 110

Gly Gln Gly Thr Leu Val Thr Val Ser Ser Ala Ser Thr Lys Gly Pro
                       115                 120                 125

Ser Val Phe Pro Leu Ala Pro Cys Ser Arg Ser Thr Ser Glu Ser Thr
                       130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                       165                 170                 175

Ala Val Leu Gln Ser Ser Gly Leu Tyr Ser Leu Ser Ser Val Val Thr
                       180                 185                 190

Val Pro Ser Ser Ser Leu Gly Thr Lys Thr Tyr Thr Cys Asn Val Asp
                       195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Phe Glu Gly Gly Pro
        225                 230                 235                 240

Ser Val Phe Leu Phe Pro Pro Lys Pro Lys Asp Thr Leu Met Ile Ser
                       245                 250                 255

Arg Thr Pro Glu Val Thr Cys Val Val Val Asp Val Ser Gln Glu Asp
                       260                 265                 270

Pro Glu Val Gln Phe Asn Trp Tyr Val Asp Gly Val Glu Val His Asn
                       275                 280                 285

Ala Lys Thr Lys Pro Arg Glu Glu Gln Phe Asn Ser Thr Tyr Arg Val
                       290                 295                 300

Val Ser Val Leu Thr Val Leu His Gln Asp Trp Leu Asn Gly Lys Glu
        305                 310                 315                 320

Tyr Lys Cys Lys Val Ser Asn Lys Gly Leu Pro Ser Ser Ile Glu Lys
                       325                 330                 335

Thr Ile Ser Lys Ala Lys Gly Gln Pro Arg Glu Pro Gln Val Tyr Thr
                       340                 345                 350

Leu Pro Pro Ser Gln Glu Glu Met Thr Lys Asn Gln Val Ser Leu Thr
                       355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Tyr Ser Arg Leu Thr Val Asp Lys
                       405                 410                 415

Ser Arg Trp Gln Glu Gly Asn Val Phe Ser Cys Ser Val Met His Glu
                       420                 425                 430

Ala Leu His Asn His Tyr Thr Gln Lys Ser Leu Ser Leu Ser Leu Gly
                       435                 440                 445

Lys

<210> SEQ ID NO 29
<211> LENGTH: 214
<212> TYPE: PRT
<213> ORGANISM: Artificial sequence
<220> FEATURE:
```

<223> OTHER INFORMATION: NKTT120 AND NKTT320 Light chain sequence
     (Translation of VK4-CK)

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Tyr Cys Gln Gln His Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 452
<212> TYPE: PRT
<213> ORGANISM: Artificial sequence
<220> FEATURE:
<223> OTHER INFORMATION: 6B11 Chimeric IgG1 Heavy Chain

<400> SEQUENCE: 30

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Asn Gly Asn Tyr Val Asp Tyr Ala Met Asp Tyr Trp
            100                 105                 110

Gly Gln Gly Thr Ser Val Thr Val Ser Ser Ala Ser Thr Lys Gly Pro

```
                115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Arg Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
            435                 440                 445
Ser Pro Gly Lys
        450

<210> SEQ ID NO 31
<211> LENGTH: 214
<212> TYPE: PRT
<213> ORGANISM: Artificial sequence
<220> FEATURE:
<223> OTHER INFORMATION: 6B11 Chimeric Ck Light Chain

<400> SEQUENCE: 31

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
```

-continued

```
                     20                  25                  30
Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
        210
```

HUMANIZED ANTIBODIES TO INKT

RELATED APPLICATIONS

This application claims the benefit under 35 U.S.C. § 119(e) of U.S. provisional application Ser. No. 61/552,337, filed Oct. 27, 2011, the content of which is incorporated by reference herein in its entirety.

BACKGROUND OF THE INVENTION

Asthma is a relatively common illness worldwide. In 2009, the Centers for Disease Control estimated the asthma prevalence rate in the U.S. to be 8.2% of the population or 24.6 million people. Worldwide the burden of asthma is large, with an estimated prevalence of over 300 million cases and this number is expected to grow by more than 100 million cases by 2025.

Asthma is one of the country's most costly illnesses. The annual U.S. expenditures for health and lost productivity due to asthma are estimated at over $20 billion. In 2006 and 2007 in the U.S. there were approximately 3500 asthma-related deaths per year and over 250,000 deaths worldwide.

Asthma severity is classified according to the frequency and severity of symptoms, or "attacks", the results of pulmonary function tests and the level of medications required to gain control of symptoms (NIH, "*Guidelines for the Diagnosis and Management of Asthma*, 2007"). Approximately 30% of asthma patients have mild, intermittent symptoms of asthma with normal pulmonary function tests. Another 30% of asthma patients have mild, persistent symptoms (two or more episodes per week) with normal pulmonary function tests. Forty percent of asthma patients have moderate-to-moderate-severe, persistent daily or continuous symptoms of asthma with abnormal pulmonary function tests. It is estimated that over 80% of the asthma-related health care costs are due to 20% of individuals with moderate-to-moderate-severe persistent and/or milder, treatment-refractory asthma. Thus, treatment-refractory asthma remains a significant unmet medical need.

Modulating the immune system has been pursued as a desirable approach to treat asthma, as well as a variety of other diseases and disorders, including, but not limited to, autoimmune disease, infection, allergy, inflammatory conditions, spontaneous abortion, pregnancy, graft versus host disease and cancer. T cells have been a target of such modulation. T cells are lymphocytes that participate in multiple immune system functions. Subsets of T cells such as helper T cells, cytotoxic T cells and suppresser T cells, mediate different immunologic functions. Natural killer T (NKT) cells are a subset of T lymphocytes that share surface markers and functional characteristics with both conventional T cells and natural killer (NK) cells. Unlike T cells, they recognize glycolipid antigens rather than peptide antigens.

NKT cells can be divided into three subsets: Type 1 which express an invariant T cell receptor and are CD1d-restricted (iNKT), Type 2 (NKT) which express varied T cell receptors, but are CD1d-restricted, and Type 3 which express varied T cell receptors and are not CD1d-restricted (NKT-like). Type 1 iNKT cells express a uniquely rearranged, highly conserved, semi-invariant TCR-α chain (Vα24-Jα18 in humans and Vα14-Jα18 in mice), which preferentially pairs with specific TCR-β chains (Vβ11 in humans or Vβ8.2, Vβ7 and Vβ2 in mice). They are highly conserved throughout animal phylogeny. This is in contrast to most T cell subpopulations, which have diverse sequences for their T Cell Receptors (TCRs). The invariant TCR of iNKT cells reacts with glycolipid antigens presented on the MHC-I-like protein CD1d on the surface of antigen presenting cells. A hallmark of iNKT cells is their capacity to rapidly produced a mixture of cytokines, including IL-4 and IFNγ, which are signature cytokines otherwise produced by T helper type I (Th1) and Th2 cells, respectively. Invariant NKT cells are sometimes referred to as "Classical NKT Cells".

A unique feature of iNKT cells is that they recognize the marine sponge-derived glycolipid, α-Galactosyl-Ceramide (α-GalCer), presented on CD1d. This has been utilized to monitor mouse, non-human primate (NHP), and human iNKT cells by flow cytometry, by using α-GalCer-loaded CD1d tetramers. The mouse monoclonal antibody 6B11, which binds to the invariant loop of the human-iTCR, has also been used to monitor human and NHP iNKT cells.

iNKT cells represent a very small subset of the total T cell population in human and non-human peripheral blood. Their relative numbers can vary over one hundred-fold between normal individuals, representing anywhere from 0.01% to over 1% of $CD3^+$ cells in humans, where the low end of the range represents the majority of humans.

Conventional T cells require exposure to foreign antigen in order to mature and acquire memory phenotype. Clonally-expanded populations of conventional memory T cells that are depleted through pathological events, or by pharmacological intervention, can only recover when new thymic emigrants, with identically rearranged TCRs, are exposed to similar or identical foreign or pathogenic antigen as the original insult. Such depletion of T cells can create a "hole" within the immune repertoire for a given individual. Unlike conventional T cells, iNKT cells have a continuous regenerative capacity. In humans, iNKT cell regeneration has been studied following bone marrow transplantation. Full recovery of iNKT cell numbers to baseline has been observed one month following peripheral blood stem cell transplant rescue for ablative therapy. iNKT cell depletion therapy, therefore, could be less risky than depleting other T cells.

iNKT cells develop in the thymus, similar to other T cells. Studies in mice show that iNKT cells, unlike conventional T cells, acquired a memory phenotype during their natural development by recognizing hitherto unknown, endogenous antigens presented on CD1d molecules, and without requiring prior exposure to foreign or pathogenic antigens. Due to their memory phenotype, they can be rapidly activated and expand within the peripheral immune compartment in response to exposure to foreign or endogenous glycolipid antigens presented by antigen-presenting cells (APCs).

iNKT cells share characteristics of both the innate and adaptive arms of the immune system and thus play a unique role by modulating T and B cell responses as well as innate immunity (1). iNKT cells are rapid-onset which is a feature of the innate immune system. They also display features of the adaptive immune system because they share properties of other T cells such as antigen specific responses. As such, they serve as a bridge between the two systems where they can play both pro-inflammatory and immuno-regulatory roles either to enhance or attenuate developing immune responses, respectively (2).

The properties of iNKT cells has prompted investigations into the manipulation of iNKT cell function as a treatment for disease (3, 4, 5, 6). Numerous studies have shown that iNKT cells can regulate the balance between Th1 and Th2 responses. These cells are postulated to play a role in the response to pathogens, in immune surveillance in cancer, and in the regulation of autoimmunity. For most of these conditions, the iNKT cell defect has only been partially characterized and in some cases has been disputed by contradictory studies. Human studies, in particular, are constrained by two important limitations. First, most human studies have used suboptimal methods for the identification of iNKT cells. Second, most human studies are qualitative only, and little human data exists respecting the functional consequences of modulation of iNKT cell numbers, ratios, or function.

iNKT cell function has received significant attention concerning its potential role in asthma. Inhibition of iNKT cell function, either through genetic ablation of iNKT cells, or through pharmacologic blockade, blocks the development of airway hyper-responsiveness (AHR) in mice (7, 8). This is seen with both ovalbumin- and ozone-induced AHR (9). iNKT cells increase in the lungs of wild type mice following exposure to ovalbumin or ozone. In mice that are genetically devoid of iNKT cell function, through knockout of the gene encoding a portion of the invariant T cell receptor, adoptive transfer of iNKT cells restores the ability for allergens to induce AHR (9). Conversely, activation of iNKT cells in the airways with the potent iNKT cell agonist, α-GalCer, induces a response indistinguishable from AHR in both mice and non-human primates (10, 11). Mice genetically devoid of iNKT cells are also resistant to development of pathologic changes in the airways in a chronic Sendai virus model of COPD (12). Similar to the findings from the murine models, in humans, iNKT cells are not present in the lungs of healthy individuals, but they are present in the lungs of patients with mild-to-moderate asthma, and they increase further after allergen or viral challenge (3, 13, 14). There appears to be little or no correlation between the levels of iNKT cells in the BAL fluid and the peripheral blood of patients with asthma. The prior art has not established whether iNKT cells are causally connected to asthma or are the result of asthma or whether a therapy aimed at blocking iNKT cell function could be a treatment for asthma.

The mouse monoclonal antibody 6B11, which recognizes the human invariant T cell receptor, is the subject of US published application No. 2007/0160600. This antibody selectively binds human iNKT cells, being able to distinguish iNKT cells from other lymphocytes and other human tissue types. The application offers conflicting statements as to whether the 6B11 antibody would enhance or suppress an immune response. The application indicates at one point that the antibody stimulates proliferation of iNKT cells, suggesting that the antibody is an agonist of iNKT cells. The application suggests at another point that an increase in iNKT activity can result in a suppression of an immune response. At still another point, the application indicates that interfering with iNKT activity will suppress an immune response. In particular, the application suggests that an antibody should be coupled to a toxin to deplete iNKT cells in order to suppress an immune response. This application, therefore, does not make clear the medical circumstances in which use of the 6B11 antibody would be desirable.

SUMMARY OF THE INVENTION

It has been discovered, surprisingly, that certain naked antibodies which selectively bind to iNKT will transiently deplete iNKT cells at low doses in vivo. It further has been discovered that certain antibodies which selectively bind to iNKT will activate iNKT cells. Humanized antibodies that bind selectively human iNKT cells with unexpectedly high affinities also have been discovered. Based on these discoveries, it is believed that airway hyper-reactivity conditions can be treated (e.g., asthma (including, but not limited to, allergic asthma) and Chronic Obstructive Pulmonary Disease (COPD)). It further is believed that a variety of other iNKT cell mediated conditions can be treated, such as, for example, allergy, autoimmune diseases, inflammatory conditions other than allergy, ischemia reperfusion injury, sickle cell anemia, vasculitic diseases, transplant rejection, infectious diseases and cancer.

According to one aspect of the invention, a method of treatment to suppress iNKT cell function is provided. According to one aspect of the invention, a method of treatment to suppress an immune response is provided. Each method involves administering to a subject in need of treatment a naked antibody that binds selectively iNKT cells in an amount effective to suppress iNKT cell function. In some embodiments, the antibody is a depleting antibody and the amount is effective to deplete iNKT cells.

The foregoing methods can be used to treat a variety of disorders. In one aspect, the subject's immune response to an antigen is suppressed. The antigen can be, for example, an allergen, an auto-antigen or a transplant antigen. In one aspect of the invention, the subject has asthma and the treatment suppresses in the subject one or more symptoms of asthma. In some embodiments, the asthma is allergic asthma. In some embodiments, the subject has (i) mild persistent symptoms of asthma (two or more episodes per week) with normal pulmonary function tests, (ii) moderate-to-moderate-severe, persistent daily or continuous symptoms of asthma with abnormal pulmonary function tests, or (iii) treatment-refractory asthma. In one aspect, the method suppresses airway remodeling in the subject. In another aspect of the invention, the subject has COPD and the treatment suppresses in the subject one or more symptoms of COPD. In one aspect the treatment suppresses airway remodeling in the subject with COPD. In one aspect the treatment slows disease progression in the subject. In another aspect, the subject has an allergy, autoimmune disease, inflammatory condition other than allergy, an ischemia reperfusion injury, sickle cell anemia, or a vasculitic diseases, and the treatment suppresses in the subject one or more symptoms of the disease. In another aspect, the subject has received or is a candidate to receive a transplant, and the treatment suppresses one or more symptoms of transplant rejection. In another aspect, the subject has an infection, and the treatment slows the growth of, halts the growth of, or kills the involved infectious agent or suppresses in the subject one or more symptoms of the infection. In another aspect, the subject has cancer, and the treatment slows the growth of, halts the growth of, or kills the cancer or suppresses in the subject one or more symptoms of the cancer. In any of the forgoing aspects and embodiments, the subject can be human and the antibody can be a humanized antibody. In any of the forgoing aspects and embodiments, the subject can be human and the antibody can be a fully human antibody. A fully human antibody is an antibody consisting only of human amino acid sequences. In some embodiments, the fully human antibody is a composite of human amino acid sequence segments from different human antibodies.

The invention involves the use of antibodies, the nature of which is described in detail below. The antibodies in some embodiments are humanized antibodies. The antibodies in some embodiments are whole, fully human antibodies. The antibodies in some embodiments can be whole fully human, composite antibodies. In some embodiments, the antibodies can have three light-chain CDR and three heavy-chain-CDR regions, and wherein each of the three light-chain CDR and three heavy-chain-CDR regions is a composite of human sequences.

The invention in another aspect involves humanized antibodies that bind with at least a certain affinity to iNKT cells. In some embodiments, the antibody binds iNKT cells with an IC50 that is less than 1.0 µg/ml for binding to recombinant soluble human iTCR. In some embodiments, the heavy chain variable region and the light chain variable region of the humanized antibodies consist of human sequences.

In some embodiments, the antibody binds the epitope defined by SEQ ID No. 1. In some embodiments, the antibody binds the epitope defined by SEQ ID No. 2. In some embodiments, the antibody has a light chain variable region comprising SEQ ID Nos. 24, 25 and 26. In some embodiments, the antibody has a light chain variable region comprising SEQ ID Nos. 24, 25 and 26 and also has a leucine at position 85. In some embodiments, the antibody has a heavy chain variable region comprising SEQ ID Nos. 21, 22 and 23. In some embodiments, the antibody has a heavy chain variable region comprising SEQ ID Nos. 21, 22 and 23 and also has a valine at position 23 and/or a threonine at position 93. In some embodiments, the antibody comprises a heavy chain variable region selected from SEQ ID Nos. 7, 8, 9, 10, 11, 12, 13 or 14. In some embodiments, the antibody comprises a light chain variable region selected from SEQ ID Nos. 15, 16, 17, 18, 19 or 20. In some embodiments, the antibody comprises a light chain variable region selected from SEQ ID Nos. 15, 16, 17, 18, 19 or 20 and a heavy chain variable region selected from SEQ ID Nos. 7, 8, 9, 10, 11, 12, 13 or 14. In some embodiments, the antibody comprises SEQ ID Nos. 10 and 18. In some embodiments, the antibody comprises SEQ ID No. 27. In some embodiments, the antibody comprises SEQ ID No. 28. In some embodiments, the antibody comprises SEQ ID No. 29. In some embodiments, the antibody comprises SEQ ID Nos. 27 and 29. In some embodiments, the antibody comprises SEQ ID Nos. 28 and 29.

According to another aspect of the invention, an isolated, humanized antibody is provided. The antibody selectively binds iNKT cells, wherein the antibody has an IC50 of less than 0.9 µg/ml for binding to recombinant soluble, human iTCR. In some embodiments, the IC50 is less than 0.8 µg/ml, less than 0.5 µg/ml, and even less than 0.3 µg/ml. In some embodiments, the IC50 is between 0.1 and 0.9 µg/ml. In some embodiments, the IC50 is between 0.1 and 0.5 µg/ml.

In some embodiments, the antibody binds the epitope defined by SEQ ID No. 1. In other embodiments, the antibody binds the epitope defined by SEQ ID No. 2. In some embodiments, the antibody has three light-chain CDR regions and three heavy-chain CDR regions, and wherein each of the three light-chain and three heavy-chain CDR regions is a composite of human sequences.

In some embodiments, the antibody has a light chain variable region comprising SEQ ID Nos. 24, 25 and 26. In some embodiments, the antibody has a light chain variable region comprising SEQ ID Nos. 24, 25 and 26 and also has a leucine at position 85. In some embodiments, the antibody has a heavy chain variable region comprising SEQ ID Nos. 21, 22 and 23. In some embodiments, the antibody has a heavy chain variable region comprising SEQ ID Nos. 21, 22 and 23 and also has a valine at position 23 and/or a threonine at position 99. In some embodiments, the antibody comprises a heavy chain variable region selected from SEQ ID Nos. 7, 8, 9, 10, 11, 12, 13 or 14. In some embodiments, the antibody comprises a light chain variable region selected from SEQ ID Nos. 15, 16, 17, 18, 19 or 20. In some embodiments, the antibody comprises a light chain variable region selected from SEQ ID Nos. 15, 16, 17, 18, 19 or 20 and a heavy chain variable region selected from SEQ ID Nos. 7, 8, 9, 10, 11, 12, 13 or 14. In some embodiments, the antibody comprises SEQ ID Nos. 10 and 18. In some embodiments, the antibody comprises SEQ ID No. 27. In some embodiments, the antibody comprises SEQ ID No. 28. In some embodiments, the antibody comprises SEQ ID No. 29. In some embodiments, the antibody comprises SEQ ID Nos. 27 and 29. In some embodiments, the antibody comprises SEQ ID Nos. 28 and 29.

In some embodiments the antibody binding region is non-reactive with human peripheral blood monocytes of all human haplotypes.

In any of the foregoing embodiments, the humanized antibody may be a depleting antibody. In any of the foregoing embodiments, the humanized antibody may be an activating antibody. In any of the of the foregoing embodiments, the antibody may have the property of inducing [induces] no significant change in one or more serum cytokine levels after administration to the subject.

The invention in another aspect is a method. The method involves contacting iNKT cells of a subject with an isolated humanized antibody that selectively binds iNKT cells in an amount effective to block the activity of the iNKT cells or to deplete the iNKT cells. In one embodiment, the cells are contacted in vitro. In one embodiment, the cells are contacted in vivo, and the amount is an amount sufficient to suppress an immune response in the subject. In one embodiment, the antibody is a depleting antibody and the amount is sufficient to deplete iNKT cells in the subject. In these embodiments, the antibodies are any of the humanized antibodies as described above, except for activating antibodies.

The invention in another aspect is a method. The method involves contacting iNKT cells of a subject with an isolated humanized antibody that selectively binds and activates iNKT cells in an amount effective to activate the iNKT cells. In one embodiment, the cells are contacted in vitro. In one embodiment, the cells are contacted in vivo, and the amount is an amount sufficient to enhance an immune response in the subject. In these embodiments, the antibodies are any of the humanized antibodies as described above, except for antibodies block the function of or deplete iNKT cells.

BRIEF DESCRIPTION OF THE DRAWINGS

FIG. 1 shows NKTT120 Binding to Human Peripheral Blood iNKT Cells. Human whole blood from three donors (26027, 26028, 26031) was stained with α-GalCer-loaded CD1d tetramer, 6B11-FITC or NKTT120-FITC in conjunction with anti-CD3 and anti-Vα24 mAbs. Red blood cells were subsequently lysed and cells analyzed by flow cytometry. Cells shown are gated on CD3+ lymphocytes.

FIG. 2 shows blocking of CD1d-tetramer Binding to iNKT Cells by NKTT120. A) Human PBMCs were incubated in presence or absence of 30 µg/ml NKTT120 for 30 minutes and then, without washing, stained with CD3 and α-GalCer-loaded CD1d-tetramer. The presence of the antibody blocks tetramer staining.

Figure 12:
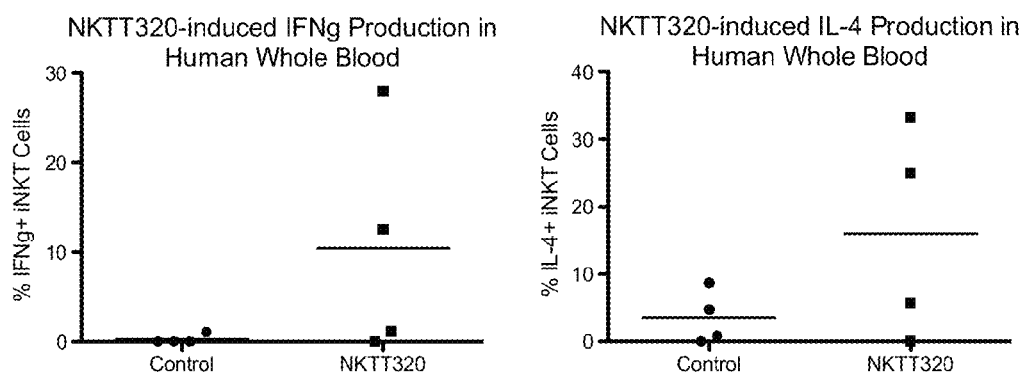

B) Human iTCR transfectant (expressing both Vα24-Jα18 and Vβ11 chain of the human iTCR) was incubated in presence or absence of 30 µg/ml NKTT120 for 30 minutes and then, without washing, stained with α-GalCer-loaded CD1d-tetramer. The presence of NKTT120 blocks binding of α-GalCer-loaded CD1d-tetramer.

FIG. 3 shows the depletion of iNKT Cells in Blood Spleen and Lymph Node by NKTT120. Vα24 transgenic Jα18-deficient mice were dosed intraperitoneally with NKTT120 (n=2 per dose) and sacrificed forty-eight hours later. Blood, spleen and lymph node lymphocytes isolated and iNKT cell numbers were subsequently determined by flow cytometry.

FIG. 4 shows time Course of iNKT Cell Depletion by NKTT120 in Vα24 Transgenic Mice.

A) Vα24 transgenic mice (n=2 per group) were injected intraperitoneally with 100 μg of NKTT120 and sacrificed at indicated time points. Gating on splenic CD3+NK1.1+ iNKT cells, the percentage of 6B11 binding cells was assessed.

B) Vα24 transgenic mice (n=2 per group) were injected with 100 μg NKTT120. A control group did not receive NKTT120. Forty-eight hours later, separate NKTT120-treated mice and control mice were injected with 2 μg α-GalCer. Two hours after α-GalCer injection, mice were sacrificed and splenic CD3+NK1.1+ iNKT cells were assayed for intracellular IFNγ by flow cytometry.

FIG. 5 shows that pharmacologic Depletion of iNKT Cells in Vα24 Transgenic Mice Abrogates a-GalCer-Mediated iNKT Cell-dependent AHR. Vα24 transgenic mice, backcrossed to BALB/c n=6 (n=3 per group), were injected intraperitoneally with 100 μg of NKTT103 or Rituximab. Forty-eight hours later, mice were challenged with 1 μg of α-GalCer. After an additional 24 hours, mice were challenged with methacoline and lung resistance (RL) and dynamic compliance (Cdyn, not shown) were assessed. Rituximab was used as a negative isotype control.

FIG. 6 shows the Comparison of Human and Cynomolgus Monkey iNKT Cell Frequencies. Cynomolgus monkey frequency range of iNKT cells, as determined by CD3, anti-Vα24 (Clone C15) and 6B11 binding, in peripheral blood is strikingly comparable to that found in human subjects.

FIG. 7 shows the Comparison of Saturation binding to Human and Cynomolgus Monkey iNKT cells. Cynomolgus monkey (NHP) and human iNKT cells demonstrate similar saturation binding of NKTT120 in a direct competitive binding assay. Cynomolgus monkey or human whole blood was incubated with indicated concentrations of NKTT120 and then stained with fluorochrome-labeled 6B11 to assess saturation binding of iNKT cells. Human samples were purchased from Research Blood Components, Inc.

FIG. 8 shows iNKT Cell Depletion by NKTT120 24 Hours After Dosing. Animals were treated with a single dose of NKTT120 and monitored for seven days. Data show a dose-dependent decrease in iNKT cells 24 hours after treatment (n=1 per dose). The pretreatment baseline iNKT levels in this cohort of animals ranged from 0.12%-1.13% of CD3+ cells. Complete depletion of iNKT cells was seen at 24 hours following dosing with the 0.03 mg/kg dose.

FIG. 9 shows iNKT Cell Depletion by NKTT120 in Cynomolgus Monkeys. NKTT120 dose response of the depletion of iNKT cells in cynomolgus monkeys.

FIG. 10 shows the Effect of NKTT120 on iNKT, B and T Cells. NKTT120 (0.03 mg/kg) treatment has no significant effect on B cells and other T cells.

FIG. 11 shows the Effect of NKTT120 Cytokine Levels in Human Whole Blood. Cytokine levels in untreated, NKTT120- and anti-CD3-treated whole blood samples from healthy donors (n=4). Only results that differed from control levels are shown. Blood samples from healthy donors were purchased from Research Blood Components, Inc.

FIG. 12 shows iNKT cell activation by anti-iNKT mAbs with reduced Fc-effector function.

DETAILED DESCRIPTION

The following detailed description is made by way of illustration of certain aspects of the invention. It is to be understood that other aspects are contemplated and may be made without departing from the scope or spirit of the present disclosure. The following detailed description, therefore, is not to be taken in a limiting sense. Scientific and technical terms used herein have meanings commonly used in the art unless otherwise specified. The definitions provided herein are to facilitate understanding of certain terms used frequently herein and are not meant to limit the scope of the present disclosure. The singular forms "a", "an", and "the" encompass the plural, unless the content clearly dictates otherwise. The term "or" is generally employed in its sense including "and/or" unless the content clearly dictates otherwise.

The invention in one aspect is antibodies as described herein, useful for a variety of purposes. The antibodies can be used to identify the presence of iNKT cells in a biological sample. They can be used to deliver an agent attached to the antibodies to an iNKT cell, in vitro or in vivo. Such agents may be covalently or non-covalently attached, and include, for example, labels, toxins, co-stimulatory molecules and the like. The antibodies can be used to interfere with or block the activity of iNKT cells. Depleting antibodies can be used to deplete iNKT cells from a population of cells in vitro or in vivo. Activating antibodies can be used to activate iNKT cells in vitro or in vivo. The antibodies also can be used to treat a variety of medical conditions, particularly medical conditions in humans. In the case of blocking or depleting antibodies, it is believed that the antibodies can be used to treat asthma, COPD, allergy, inflammatory conditions other than allergy, transplant rejection, ischemic reperfusion injury, sickle cell disease, and autoimmune diseases. In the case of activating antibodies, it is believed that the antibodies can be used, for example, to treat cancer and infectious disease.

"Activating Antibody" is an antibody that, when it binds to an iNKT cell in vivo, results in stimulating the iNKT cell to produce interferon gamma, IL 4, IL10, or IL 13 versus blocking the activity of or depleting the iNKT cell. Activating Antibodies typically have no Fc portion or have an Fc portion that does not bind FcγRI and C1q. In one embodiment, the Fc portion of the Activating Antibody does not bind FcγRI, C1q, or FcγRIII. Antibodies with such functionality, in general, are known. There are native such antibodies, such as antibodies with an IgG4 Fc region. There also are antibodies with Fc portions genetically or chemically altered to eliminate the Antibody dependent cell cytotoxicity (ADCC) and/or complement dependent cytotoxicity (CDC) functionality.

"Allergy" refers to abnormal immune responses to a substance (allergen or environmental antigen). Allergy is typically an episodic condition associated with the production of antibodies from a particular class of immunoglobulin, IgE, against allergens. Symptoms of an allergic reaction vary, depending on the location within the body where the IgE reacts with the antigen. If the reaction occurs along the respiratory epithelium, the symptoms generally are sneezing, coughing and asthmatic reactions.

"Allergen" means a substance that can induce an allergic or asthmatic response in a susceptible subject. The list of allergens is enormous and can include pollens, plants, insects (including venoms), animals (including animal dander), fungal spores, and drugs) as well as environmental antigens or irritants (e.g. smoke, smog, ozone, hydrocarbons, dust, cold).

"Asthma" refers to a disorder of the respiratory system characterized by inflammation and narrowing of the airways, and increased reactivity of the airways to inhaled agents. Asthma is frequently, although not exclusively, associated with an atopic or allergic condition. Symptoms of asthma include recurrent episodes of wheezing, breathlessness, chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, eosinophils, and lymphocytes. As a result of the airway inflammation, asthma patients often experience airway hyper-responsiveness (AHR), airflow limitation, respiratory symptoms, and disease chronicity. Airflow limitations include acute bronchoconstriction, airway edema, mucous plug formation, and airway remodeling, features which often lead to bronchial obstruction.

"Blocking Antibody" is an antibody that, when it binds to an iNKT cell in vivo, results in preventing or lessening the ability of the iNKT cell to produce interferon gamma, IL 4, IL10, and IL 13. Blocking Antibodies include Depleting Antibodies.

"Composite antibody" is an antibody that contains sequence segments from different antibodies.

"Depleting antibody" is an antibody that, when it binds to an iNKT cell in vivo, results in elimination of iNKT cells. The elimination need not be complete elimination. Instead, elimination embraces a detectable reduction in iNKT cells. The reduction may be, for example, a reduction in iNKT cells by 10%, 20%, 30%, 40%, 50%, 60%, 75% or more. Depleting antibodies typically have an Fc portion that binds FcγRI and/or C1q. In one embodiment, the Fc portion of the depleting antibody binds FcγRI, C1q, and FcγRIII Antibodies with such functionality, in general, are known. There are native such antibodies, such as antibodies with an IgG1 Fc region. There also are antibodies with Fc portions genetically or chemically altered to enhance the ADCC and/or CDC functionality.

"Enhance an immune response", in general, means to increase the production of interferon gamma, IL4, IL10 or IL13 by iNKT cells, to increase the surface expression of chemokine receptors or to cause the iNKT cells to proliferate. In connection with a specific disease or condition, "enhance an immune response" means to halt the development of, inhibit the progression of, reverse the development of, or otherwise reduce or ameliorate one or more symptoms of the disease or condition, for example, one or more symptoms of cancer or infectious disease.

"Isolated" means, in the context of an antibody (or nucleic acid molecule encoding an antibody), the antibody (or nucleic acid) has been removed from its natural milieu or has been altered from its natural state. As such, "isolated" does not necessarily reflect the extent to which the antibody or nucleic acid molecule has been removed from its natural milieu or has been altered from its natural state. However, it will be understood that an antibody or nucleic acid molecule that has been purified to some degree is "isolated".

"Subject" means a mammal, such as a human, a nonhuman primate, a dog, a cat, a sheep, a horse, a cow, a pig or a goat. In an important embodiment, the mammal is a human.

"Suppress iNKT cell function", in general, means to decrease the activity of iNKT cells by inhibiting the activity of or depleting iNKT cells. In connection with a specific disease or condition, "suppress iNKT cell function" means to halt the development of, inhibit the progression of, reverse the development of, or otherwise reduce or ameliorate one or more symptoms of the disease or condition, for example, one or more symptoms of asthma (including allergic asthma), COPD, allergy, inflammatory diseases other than allergy, graft versus host disease, graft rejection, ischemic reperfusion injury and autoimmune disease.

The methods herein employ antibodies. The antibodies bind selectively iNKT cells. An antibody that binds selectively iNKT cells means it has the ability to be used in vitro or in vivo to bind to and distinguish iNKT cells of a species from other tissue types of the species, including other NKT types, other lymphocyte types, and all other tissue types under the conditions in which the antibody is used, such as under physiologic conditions. In an embodiment, the antibody binds selectively human iNKT cells. In an embodiment, the antibody binds to the CDR3 loop of iNKT cells. In an embodiment, the antibody binds selectively the epitope defined by SEQ ID No. 1. In other embodiments, the antibody binds selectively the epitope defined by both SEQ ID Nos. 1 and 2.

In some embodiments, the antibody is a naked antibody. A "naked antibody" means an antibody that includes an antigen-binding fragment, but does not have attached to it a separate effector molecule, such as a toxin. Naked antibodies in some embodiments are whole monoclonal antibodies. Naked antibodies in some embodiments are humanized monoclonal antibodies. Naked antibodies in some embodiments are fully human monoclonal antibodies. The Fc region of the naked antibody may be modified, for example, such that the antibody has an improved half-life or an improved ability to mediate ADCC. In some embodiments, the Fc region of the naked antibody may be modified, for example, such that the antibody has a decreased ability to mediate ADCC. The naked antibody may be produced in mammalian or non-mammalian cells, and therefore may have various glycosylation patterns.

The term "antibody" is used in the broadest sense and specifically includes, for example, single monoclonal antibodies, antibody compositions with polyepitopic specificity, single chain antibodies, and antigen-binding fragments of antibodies. An antibody may include an immunoglobulin constant domain from any immunoglobulin, such as IgG1, IgG2, IgG3, or IgG4 subtypes, IgA (including IgA1 and IgA2), IgE, IgD or IgM. In some embodiments, the constant domain is one that mediates antigen dependent cellular cytotoxicity (ADCC) or complement-dependent cytotoxicity (CDC).

As used herein, an "antigen-binding fragment" means a portion of an intact antibody that binds antigen. Examples of antibody fragments include Fab, Fab', F(ab')$_2$, and Fv fragments; diabodies; linear antibodies (Zapata et al., Protein Eng. 8 (10): 1057-1062 [1995]); and single-chain antibody molecules.

"Fv" is the minimum antibody fragment containing a complete antigen-recognition binding site. This region consists of a dimer of one heavy- and one light-chain variable domain in tight, non-covalent association. In this configuration the three CDRs of each variable domain interact to define an antigen-binding site on the surface of the $V_H$-$V_L$ dimer. Collectively, the six CDRs confer antigen-binding specificity to the antibody.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

"Single-chain Fv" or "sFv" antibody fragments include the $V_H$ and $V_L$ domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term hybridoma describes the combination of a B cell that can recognize a particular antigen and a myeloma cell that lives indefinitely to make the hybridoma cell a kind of perpetual monoclonal antibody-producing factory. Such antibodies are generated from animal cells, typically the mouse. If a mouse monoclonal antibody is used to treat a different species, such as a human, the human's immune system will recognize the mouse antibodies as 'foreign' and mount an immune reaction against them. To circumvent this immune reaction, the part of the mouse antibody recognized by the human immune system can be replaced genetically with parts from a human antibody. The product of this mouse-human antibody gene is called a "humanized" monoclonal antibody. This product looks enough like a normal human antibody to avoid being recognized and destroyed by the patient's own immune system. This avoids eliciting a potentially harmful immune response if the antibody is used therapeutically in a human.

In some embodiments, the antibody does not elicit an immune response when administered to a human. In this manner, it can be administered more than once, in some embodiments several of more times annually, without generating an unwanted immune response that would interfere with the subsequent administrations. As used herein in connection with humanized antibodies, "does not elicit an immune response" means does not generate a cytokine response above background when contacted with a panel of human PBMCs representing the diversity of human haplotypes. Such a test is detailed in the examples below.

Humanized forms of non-human (e.g., murine) antibodies then are chimeric immunoglobulins, immunoglobulin chains or fragments thereof (such as Fv, Fab, Fab', F(ab')2, scFv or other antigen-binding subsequences of antibodies) which contain minimal sequence derived from the non-human immunoglobulin. Humanized antibodies typically include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies can reduce antigenicity. According to the "best-fit" method, the sequence of the variable domain of a rodent antibody is screened against the entire library of known human variable domain sequences. The human sequence or combination of sequences closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

In an embodiment, as described in the examples below, a CDR region is made from a composite of overlapping human sequences, with one segment of the CDR found in one human sequence and another segment of the same CDR found in another human sequence, each of the two sequences having common sequences at an overlapping region where the segments meet. In an embodiment, the composite human sequence is free of known T cell epitopes. In an embodiment, as described in the examples below, the composite human sequence does not elicit an immune response in humans.

It is further important that antibodies be humanized with retention of high affinity for the antigen and other favorable biological properties. In this regard, there may be amino acids outside the CDRs, which contribute to the affinity of the antibody, and including these residues can be important to having an antibody of acceptable affinity. As used herein, a consensus sequence of a variable region is that portion of the variable region including the CDRs and certain other 'framework' residues believed to be important to conferring antigen binding specificity and which are to be included in a humanized antibody. Residues not included in the consensus sequence are more likely substitutable without substantial reduction in the antibody's affinity for iNKT cells. Consensus sequences are chosen using, for example, three dimensional models of the parental and humanized sequences. Computer programs also are available which illustrate and display probable three-dimensional conformational structures of selected candidate immunoglobulin sequences. Inspection of these displays permits analysis of the potential role of the residues in the functioning of the candidate immunoglobulin sequence, i.e., the analysis of residues that influence the ability of the candidate immunoglobulin to bind its antigen.

Transgenic animals (e.g., mice) that are capable, upon immunization, of producing a full repertoire of human antibodies in the absence of endogenous immunoglobulin production can be employed as well. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immunol., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985)0; Boerner et al., J. Immunol., 147(1):86-95 (1991)).

Without wishing to be bound by any theory of the invention, it is believed that the naked blocking antibodies of the invention not only interfere with the activity of iNKT cells when administered, but rather result in a depletion of iNKT cells. It also is believed that this depletion is transient, with iNKT cell populations being restored over time. It is believed that the depletion of iNKT cells is mediated by ADCC. In this manner, surprisingly, naked antibodies can be used to suppress immune responses mediated by iNKT cells. It is believed that such immune responses include asthma (including allergic asthma), chronic obstructive, pulmonary disease (COPD), allergy, autoimmune diseases, inflammatory conditions other than allergy, ischemia reperfusion injury, vasculitic diseases, and transplant rejection.

In one embodiment, the antibodies are produced in CHO cells. It has been discovered that naked antibodies produced in CHO cells are effective in depleting iNKT cells, notwithstanding CHO cells are not considered to have an optimal glycosylation pattern for ADCC. These antibodies also are effective in depleting iNKT cells, notwithstanding the lack of any enhancement to the Fc region to increase ADCC mediated depletion. That these antibodies are so effective without such enhancements is surprising.

In some embodiments, the depleting antibody induces no significant change in one or more serum cytokine levels after administration to the subject. "No significant change" means the change in the level of one or more serum cytokines in a subject is less than 25%, less than 20%, less than 15%, less than 10%, or less than 5% following administration of the depleting antibody. In some embodiments, the serum cytokine levels show no significant change up to 2 hours, 4 hours, 8 hours, 16 hours, or 24 hours following administration of the depleting antibody. Examples of serum cytokines include, but are not limited to those shown in Table 8. In some embodiments, the depleting antibody induces no significant change in the levels of one or more serum cytokine shown in Table 8. In some embodiments, the depleting antibody induces no significant change in the levels of all serum cytokines shown in Table 8. In some embodiments, the depleting antibody induces no significant change in change in the levels of any 2, 3, 4, 5, or 6 of the serum cytokines shown in Table 8. In some embodiments, the depleting antibody induces no significant change in the levels of any one or more (including all) serum IFNγ, IL-4, IL-10, IL-17, TNF-α, IL-2, IL-5, IL-8, IL-1 RA and MIP-1β.

As mentioned above, there are well known strategies for enhancing the effectiveness of antibodies. Some of these changes are via changes to the Fc region. Some involve changes to the variable region. In the latter instance, changes to the framework region can enhance ability of an antibody to bind its target. In addition, it has been demonstrated that changes to variable region can extend the half-life of an antibody. See, for example, "Reduced elimination of IgG antibodies by engineering the variable region", Hattori et al., Protein Engineering, Design and Selection, vol 23 no. 5, pp. 385-392, 2010.

In general, IgG1 has been a popular choice for an antibody that will mediate cell killing by antibody dependent cell-mediated cytotoxicity and complement activation. IgG3 has been used more sparingly, perhaps because of its somewhat shorter half-life and extensive allotypic polymorphism. IgG1 has been modified to enhance its cell-killing effector functions. For example, see U.S. Published Application 2008/008018344. One particular approach to such modifications is described in "Engineered antibody Fc variants with enhanced effector function", Dahiyat et al, PNAS, vol. 103, No 11, 4005-4010, Mar. 14, 2006. IgG4, on the other hand, has been used as an Activating Antibody, as it has a low affinity for FcgammaRI. IgG4 has been modified to decrease its Fc effector functions, making it even more suitable as an Activating Antibody. For example, an Fc region modified by two single residue substitutions is described in "Elimination of Fc Receptor-dependent Effector Function of a Modified IgG Monoclonal Antibody to Human CD4", Truneh et al., The Journal of Immunology, 1925-1933, 2000. Changes to the glycosylation of the Fc region also have been made to improve antibody based therapeutics. See for example, Glycosylation as a strategy to improve antibody-based therapeutics", Jefferis, R., Nature Reviews, Vol 8, March 2009, 226-234. All such modifications as described above are within the scope of the present invention.

In general, host cells may be transfected or transformed with cloning vectors or expression vectors for humanized antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Molecular Cloning, A Laboratory Manual, $3^{rd}$ edition, vols. 1-3, eds. Sambrook and Russel (2001) Cold Spring Harbor Laboratory Press.

Methods of eukaryotic cell transfection and prokaryotic cell transformation are known to those of ordinarily skill in the art and include, for example, $CaCl_2$, $CaPO_4$, liposome-mediated and electroporation. Depending on the host cell used, transformation is performed using standard techniques appropriate to such cells. For example, calcium treatment employing calcium chloride, as described Molecular Cloning, A Laboratory Manual, 3$^{rd}$ edition, vols. 1-3, eds. Sambrook and Russel (2001) Cold Spring Harbor Laboratory Press, or electroporation may be used for prokaryotes. For mammalian cells that do not contain cell walls, the calcium phosphate precipitation method of Graham and van der Eb, Virology, 52:456-457 (1978) may be employed. General aspects of mammalian cell host system transfections have been described in, e.g., U.S. Pat. No. 4,399,216. Transformations into yeast are typically carried out according to the method of Van Solingen et al., J. Bact., 130:946 (1977) or Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning the DNA in the vectors herein include prokaryote, yeast, or higher eukaryote cells. Suitable prokaryotes include eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. Alternatively or in addition, in vitro methods of cloning, e.g., PCR or other nucleic acid polymerase reactions are suitable.

Suitable host cells for the expression of glycosylated, humanized antibodies include those derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFP(CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is within the routine ability skill in the art.

The nucleic acid (e.g., cDNA or genomic DNA) encoding a humanized antibody (or portion thereof) may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques, which are known to those of skill in the art.

The humanized antibody (or portion thereof) may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the humanized antibody (or portion thereof)-encoding DNA that is inserted into the vector.

Expression vectors or cloning vectors may include a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter operably linked to the humanized antibody (or portion thereof)-encoding nucleic acid sequence to direct mRNA synthesis. Promoters recognized by a variety of potential host cells are well known. Promoters suitable for use with prokaryotic hosts include the beta.-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgamo (S.D.) sequence operably linked to the DNA encoding HCN or Kir2.1 channel.

Humanized antibody (or portion thereof) transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the humanized antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the humanized antibody (or portion thereof) coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a humanized antibody (or portion thereof).

For example, a viral vector, such as an adeno-associated viral (AAV) vector may be operatively linked components of control elements. For example, a typical vector includes a transcriptional initiation region, a nucleotide sequence of the protein to be expressed, and a transcriptional termination region. Typically, such an operatively linked construct will be flanked at its 5 and 3 regions with AAV ITR sequences, which are viral cis elements. The control sequences can often be provided from promoters derived from viruses such as, polyoma, Adenovirus 2, cytomegalovirus, and Simian Virus 40. Viral regulatory sequences can be chosen to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to various embodiments, the vector contains the proximal human brain natriuretic brain (hBNP) promoter that functions as a cardiac-specific promoter. For details on construction of such a vector see LaPointe et al., "Left Ventricular Targeting of Reporter Gene Expression In Vivo by Human BNP Promoter in an Adenoviral Vector," Am. J. Physiol. Heart Circ. Physiol., 283:H1439-45 (2002).

In various embodiments, a humanized antibody includes a heavy chain variable region having a consensus sequence. Consensus sequences were developed based on 6B11 and include all of the CDR regions of the 6B11 heavy chain, one or more framework residues, and, for the remaining amino acids, the antibody in one embodiment includes any sequence or composite of sequences from a human antibody. In one embodiment, the light chain consensus sequence comprises SEQ ID Nos. 24, 25 and 26 and also a leucine at position 85. In some embodiments, the heavy chain consensus sequence comprises SEQ ID Nos. 21, 22 and 23 and also has a valine at position 23 and/or a threonine at position 99. Additional desirable framework residues are high-lighted in Table 1.

In various embodiments, a humanized antibody includes a heavy chain variable region having an amino acid sequence of SEQ ID Nos.: 7, 8, 9, 10, 11, 12, 13, or 14, or an amino acid sequence having 90% or greater, 95% or greater, 98% or greater, or 99% or greater sequence identity to SEQ ID Nos.: 7, 8, 9, 10, 11, 12, 13 or 14, but always including the consensus sequence of SEQ ID Nos. 24, 25 and 26 and also a leucine at position 85. In some embodiments where the antibody includes a heavy chain variable region having an amino acid sequence having 90% or greater, 95% or greater, 98% or greater, or 99% or greater sequence identity to SEQ ID Nos.: 7, 8, 9, 10, 11, 12, 13 or 14, one or more or all of the amino acid differences are conservative substitutions. In some embodiments, the substitutions are only those present in a human antibody. The humanized antibody may further includes a light chain variable region amino acid sequence of SEQ ID Nos.: 15, 16, 17, 18, 19 or 20, 21, or an amino acid sequence having 90% or greater, 95% or greater, 98% or greater, or 99% or greater sequence identity to SEQ ID Nos.: 15, 16, 17, 18, 19 or 20, but always including the consensus sequence of SEQ ID Nos. 21, 22 and 23 and also a valine at position 23 and/or a threonine at position 99. In some embodiments where the antibody includes a light chain variable region having an amino acid sequence having 90% or greater, 95% or greater, 98% or greater, or 99% or greater sequence identity to SEQ ID Nos.: 15, 16, 17, 18, 19 or 20, one or more or all of the amino acid differences are conservative substitutions, but always including the consensus sequence of SEQ ID Nos. 21, 22 and 23 and also a valine at position 23 and/or a threonine at position 99. Any combination of such heavy chain and light chain amino acid sequences are contemplated. In some embodiments, a humanized antibody includes (i) a heavy chain variable region having an amino acid sequence of any of SEQ ID Nos.: 7, 8, 9, 10, 11, 12, 13 or 14, and (ii) a light chain variable region having an amino acid sequence of any of SEQ ID Nos.: 15, 16, 17, 18, 19 or 20.

In various embodiments, a humanized antibody includes (i) a variable heavy chain region comprising an amino acid sequence of SEQ ID NO: 27 or 28 and (ii) a variable light chain region comprising an amino acid sequence of SEQ ID NO 29:

A "conservative amino acid substitution" refers to substituting an amino acid of a polypeptide for another amino acid that is functionally similar. Such conservative amino acids may be substituted for each other in a polypeptide with a minimal disturbance to the structure or function of the polypeptide according to well-known techniques. The following five groups each contain amino acids that may be conservatively substituted for one another: Aliphatic: Glycine (G), Alanine (A), Valine (V), Leucine (L), Isoleucine (J); Aromatic: Phenylalanine (F), Tyrosine (T), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

The methods of making, cloning, expressing monoclonal antibodies (including the related vectors and cell lines) are well known to those of ordinary skill in the art. (See, e.g., U.S. publication number 2009/0175923, the disclosure of which is hereby incorporated by reference in its entirety.)

Humanized antibodies can be administered for the treatment of various disorders in the form of pharmaceutical compositions. Such compositions include the antibody and one or more other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to adversely affect the biological activity of the antibody. Examples of such diluents are distilled water, physiological phosphate-buffered saline, Ringer's solutions, dextrose solution, and Hank's solution. In addition, the pharmaceutical composition or formulation may also include other carriers or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized SEPHAROSE™ (GE Healthcare Bio-Sciences Ltd.), agarose, cellulose, and the like), polymeric amino acids, amino acid copolymers, and lipid aggregates (such as oil droplets or liposomes).

Pharmaceutical compositions may be injectable compositions. Injectable compositions include solutions, suspensions, dispersions, and the like. Injectable solutions, suspensions, dispersions, and the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Injectable compositions that include an antibody of the invention may be prepared in water, saline, isotonic saline, phosphate-buffered saline, citrate-buffered saline, and the like and may optionally mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. Isotonic agents such as sugars, buffers, or sodium chloride may be included. Prolonged absorption of the injectable compositions can be brought about by the inclusion in the composition of agents delaying absorption—for example, aluminum monostearate hydrogels and gelatin. Solubility enhancers may be added.

Sterile injectable compositions may be prepared by incorporating an antibody in the desired amount in the appropriate solvent with various other ingredients, e.g. as enumerated above, and followed by sterilization, as desired, by, for example filter sterilization. In the case of sterile powders for the preparation of sterile injectable solutions, methods of preparation include vacuum drying and freeze-drying techniques, which yield a powder of the active ingredient plus any additional desired ingredient present in a previously sterile-filtered solution. Any suitable sterilization process may be employed, such as filter sterilization, e.g. 0.22 micron filter or nanofiltration, gamma or electron beam sterilization, or pulsed white light. Other suitable sterilization processes include UtiSter (Pegasus Biologics, Irvine Calif.) and those described in, e.g., U.S. Pat. No. 6,946,098 and U.S. Pat. No. 5,730,933.

In various embodiments, the final solution is adjusted to have a pH between about 4 and about 9, between about 5 and about 7, between about 5.5 and about 6.5, or about 6. The pH of the composition may be adjusted with a pharmacologically acceptable acid, base or buffer. Hydrochloric acid is an example of a suitable acid, and sodium hydroxide is an example of a suitable base. The hydrochloric acid or sodium hydroxide may be in any suitable form, such as a 1N solution A resultant injectable solution preferably contains an amount of one or more antibodies effective to treat a disease. In various embodiments, an antibody is present in an injectable composition at a concentration between about 0.0001 mg/ml and about 50 mg/ml. In various embodiments, an antibody is present in an injectable composition at a concentration between about 0.01 mg/mL and about 10 mg/mL.

Antibodies also may be administered via other modes of administration known in the art for administering antibodies. Such modes of administration include inhalation, ingestion and topical application.

EXAMPLES

Example 1. Generation of Composite Humanized Antibodies from the 6B11 Murine Antibody Briefly, the heavy and light chain V region (VH and Vκ) sequences of the anti-iNKT receptor antibody clone 6B11 have been determined (15). Based on these sequences, Composite Human Antibodies™ (Antitope Ltd, Cambridge, UK) were produced. The Composite Human Antibodies™ have variable regions that consist of segments of human sequences, which variable regions have CDRs that are identical in sequence to the mouse antibody clone 6B11. Segments of human V region sequence for constructing the Composite Human Antibodies™ were sourced from unrelated human antibody sequence databases. Each selected sequence segment, as well as the junctions formed by the joined segments, were tested for the potential to bind to MHC class II using iTOPE™ analysis, and all final Composite Human Antibody™ sequence variants were designed to avoid T cell epitopes. Composite Human Antibody™ V region genes were generated using synthetic oligonucleotides encoding combinations of the human sequence segments. These were then cloned into vectors containing human constant regions, and antibodies were produced and tested for binding to target antigen by competition ELISA in comparison to the chimeric reference monoclonal.

More specifically, residues contained within the mouse CDRs (using both Kabat and Chothia definitions) together with a number of mouse framework residues were maintained in the Composite Human Antibodies™. To select important framework residues, structural models of the murine 6B11 antibody V regions were produced using Swiss PDB and analyzed in order to identify constraining amino acids in the V regions that were potentially important for the binding properties of the antibody.

From the above analysis, it was determined that a composite of human sequence segments from several different human antibodies could be combined to form an antibody that maintained the CDRs and selected framework residues of the 6B11 murine sequences. There could be a wide latitude of alternative human segments outside of the CDRs but only a narrow menu of possible human segments within the CDRs. All CDR regions in the Composite Human Antibody™ variants comprised more than one unrelated human sequence segment (sourced from the human sequence databases)

A large preliminary set of sequence segments that could be used to create 6B11 Composite Human Antibody variants were selected and analyzed using iTope™ (Antitope) technology for in silico analysis of peptide binding to human MHC class II alleles, and using the TCED™ (Antitope) a database of known antibody sequence-related T cell epitopes. Sequence segments that were identified as significant non-human germline binders to human MHC class II, or that scored significant hits against the TCED™ were discarded. This resulted in a reduced set of sequence segments, and combinations of these were again analyzed, to ensure that the junctions between segments did not contain potential T cell epitopes. Selected segments were then combined to produce heavy and light chain variable region sequences for synthesis. Five heavy chains and four light chains were initially designed and constructed. Additionally, further chains were designed in an attempt to increase the affinity of the humanized antibody for its target antigen based upon previous observations that variations in framework segment selection can have effects on overall affinity. For the initial VH design, the majority of sequence segments were related to human subgroup 3 antibody frameworks and for additional designs subgroup 1, 2 and 4 related segments were preferentially included. For the initial Vκ design, the majority of sequence segments were related to human subgroup 4 antibody frameworks for additional designs subgroup 1 and 2 related segments were preferentially included. In total, eight VH and six Vκ chains were constructed with sequences as detailed in Table 1. All VH chains were tested in combination with all Vκ chains, giving a total of 48 antibodies.

NKT01 Sequence Alignments:

NKT Heavy Chains:

```
                          10        20        30        40        50 2abc       60
SEQ ID NO. 7  VH1: EVKLVESGGGLVQPGGSLRLSCVASGFTFSNYWMNWVRQAPGKGLEWVAEIRLKSNNYATHYAESVKG
SEQ ID NO. 8  VH2: EVKLVESGGGLVQPGGSLRLSCVASGFTFSNYWMNWVRQAPGKGLEWVAEIRLKSNNYATHYAESVKG
SEQ ID NO. 9  VH3: EVQLVESGGGLVQPGGSLRLSCVASGFTFSNYWMNWVRQAPGKGLEWVAEIRLKSNNYATHYAESVKG
SEQ ID NO. 10 VH4: EVQLVESGGGLVQPGGSLRLSCVASGFTFSNYWMNWVRQAPGKGLEWVAEIRLKSNNYATHYAESVKG
SEQ ID NO. 11 VH5: EVQLVESGGGLVQPGGSLRLSCVASGFTFSNYWMNWVRQAPGKGLEWVAEIRLKSNNYATHYAESVKG
SEQ ID NO. 12 VH6: EVKLQESGPGLVKPPGTMSLTCVASGFTFSNYWMNWVRQPPGKGLEWVAEIRLKSNNYATHYAESVKG
SEQ ID NO. 13 VH7: EVKLVESGAEVKKPGASMKLSCVASGFTFSNYWMNWVRQAPGKGLEWVAEIRLKSNNYATHYAESVKG
SEQ ID NO. 14 VH8: EVKLKESGPALVKPTQTMTLTCVASGFTFSNYWMNWVRQPPGKALEWVAEIRLKSNNYATHYAESVKG
                                               CDR H1                CDR H2

70        80 2abc    90       100ab     110
RFTISRDDSKNTVYLQMNSLRAEDTGVYYCIRNGNYVDYAMDYWGQGTSVTVSS
RFTISRDDSKNTVYLQMNSLRAEDTGVYYCIRNGNYVDYAMDYWGQGTLVTVSS
RFTISRDDSKNTVYLQMNSLRAEDTGVYYCIRNGNYVDYAMDYWGQGTLVTVSS
RFTISRDDSKNTVYLQMNSLRAEDTAVYYCIRNGNYVDYAMDYWGQGTLVTVSS
RFTISRDNSKNTYLYQMNSLRAEDTAVYYCIRNGNYVDYAMDYWGQGTLVTVSS
RFTISRDDSKSQVSLKMSSVTAVDTGVYYCIRNGNYVDYAMDYWGQGTLVTVSS
RFTITRDDSTSTVYLEMSSLRSEDTGVYYCIRNGNYVDYAMDYWGQGTLVTVSS
RFTISRDDSKSQVVLTMTNMDPVDTGTYYCIRNGNYVDYAMDYWGQGTLVTVSS
                                  CDR H3
```

NKT Light Chains:

```
                          10        20        30        40        50        60
SEQ ID NO. 15 VK1: DIVMTQSPSFLSASVGDRVTITCKASQDVSTAVAWYQQKPGQAPRLLIYWASTRHTGVPDRFIGSGSG
SEQ ID NO. 16 VK2: DIVMTQSPSSLSASVGDRVTITCKASQDVSTAVAWYQQKPGQAPRLLIYWASTRHTGVPDRFIGSGSG
SEQ ID NO. 17 VK3: DIVMTQSPSSLSASVGDRVTITCKASQDVSTAVAWYQQKPGQAPRLLIYWASTRHTGVPSRFSGSGSG
SEQ ID NO. 18 VK4: DIQMTQSPSSLSASVGDRVTITCKASQDVSTAVAWYQQKPGQAPRLLIYWASTRHTGVPSRFSGSGSG
SEQ ID NO. 19 VK5: DIVMTQSPATLSVSPGERATLSCKASQDVSTAVAWYQQKPGQAPRLLIYWASTRHTGIPDRFIGSGSG
SEQ ID NO. 20 VK6: DIVMTQTPLSLSVTPGQPASISCKASQDVSTAVAWYLQKPGQSPQLLIYWASTRHTGVPDRFIGSGSG 70        80        90       100     6a
TDFTLTISSLQAEDFALYYCQQHYSTPWTFGQGTKLEIK
TDFTLTISSLQPEDFALYYCQQHYSTPWTFGQGTKLEIK
TDFTLTISSLQPEDFALYYCQQHYSTPWTFGQGTKLEIK
TDFTLTISSLQPEDFALYYCQQHYSTPWTFGQGTKLEIK
TDFTLTISSLQSEDFALYYCQQHYSTPWTFGQGTKLEIK
TDFTLKISRVEAEDVGLYYCQQHYSTPWTFGQGTKLEIK
```

Constraining residues are highlighted in reverse type.

All variant Composite Human Antibodies™ VH and Vκ region genes for 6B11 were synthesized using a series of overlapping oligonucleotides that were annealed, ligated and PCR amplified to give full length synthetic V regions. The assembled variants were then cloned directly into Antitope's pANT expression vector system. Two heavy chain vectors were used: IgG4PE (S228P, L235E) were used for constructs VH1 to VH5 and IgG1 was used for all constructs (VH1 to VH8), i.e. VH1 to VH5 were made as both IgG4PE and IgG1.

Initially, all combinations of composite heavy and light chains (VH1 to VH5 combined with Vκ1 to Vκ4) were made with both IgG4PE and IgG1 constant regions (i.e. a total of 40 antibodies). The vectors encoding the 40 antibodies were stably transfected into N50 cells via electroporation and selected using 200 nM methotrexate (Sigma Cat. No. M8407). Several methotrexate resistant colonies for each construct were tested for IgG expression levels using IgG1 and IgG4 ELISAs, and the best expressing lines were selected and frozen under liquid nitrogen. IgG1 expressing cell lines were expanded for antibody production and testing. Subsequently three additional VH regions (VH6 to VH 8) and two additional Vκ regions (Vκ5 and Vκ6) were constructed with an IgG1 constant region only. Stable cell lines were made, as above, for all combinations of the additional V regions and in combination with the initial V regions (i.e. 28 additional antibodies). Successful transfection and clone selection were achieved for all variants, although due to extremely slow growth and low expression levels it was not possible to take one variant, VH 6/Vκ2, to the protein purification stage within a reasonable timescale.

47 IgG1 variants for 6B11 were purified from NS0 cell culture supernatants on a Protein A sepharose column (GE Healthcare Cat. No. 110034-93) and quantified by OD280 nm using an extinction coefficient, ε (0.1%), based on the predicted amino acid sequence. The ε (0.1%) for variants containing either the VH 6 or VH 8 variant heavy chains is 1.58. For all other variants the ε (0.1%) is 1.60. Approximately 1 mg of each antibody variant was purified and lead antibodies (see below) were analyzed by reducing SDS-PAGE. Bands corresponding to the predicted sizes of the heavy and light chains were observed with no evidence of any contamination.

The binding of 47 NS0-derived 6B11 Composite Human Antibody™ variants to recombinant TCR heterodimer (Precision Antibody™) was assessed by competition ELISA. Briefly, HIS-Select™ High Sensitivity (HS) Nickel Coated Plate 96-well clear strip-well plates (Sigma Cat. No. 55688) were coated with the purified TCR heterodimer at 5 μg/ml in PBS, for 1 hour at 4° C. Dilution series of each of the Anti-iNKT Receptor Composite Human Antibody™ variants (50-0.39 μg/ml) were premixed with a constant concentration of biotinylated Anti-iNKT receptor chimeric reference antibody (3 μg/ml) in 0.05% BSA/PBS. Coated ELISA plates were washed with PBS/0.05% Tween 20 and 100 μl of the premixed antibodies added to each well. Plates were incubated for 1 hour at room temperature. Binding of biotinylated anti-iNKT receptor chimeric antibody to purified TCR heterodimer was detected using streptavidin-HRP (Sigma Cat. No. 00S5512) and TMB single solution substrate (Invitrogen Cat. No. 00-2323). After stopping the reaction with 3M HCl, absorbance was measured at 450 nm on a Dynex Technologies MRX TC II plate reader and the binding curves of the test antibodies compared against the anti-iNKT receptor chimeric reference antibody standard included on each plate. To allow for comparisons within and between experiments, IC50 values of variants were normalized against the reference antibody that was included on each plate.

Relative IC50 values of all the tested Composite Human Antibody™ variants compared to the chimeric reference antibody standard (6B11 IgG1) are shown in Table 2.

TABLE 2

Relative $IC_{50}$ values of all Composite Human Antibody ™ variants compared to chimeric 6B11 IgG1.

|      | VK1   | VK2   | VK3   | VK4   | VK5   | VK6   |
|------|-------|-------|-------|-------|-------|-------|
| VH 1 | 0.477 | 0.421 | 0.273 | 0.258 | 0.832 | 0.372 |
| VH 2 | 0.376 | 0.347 |       |       | 0.791 | 0.424 |
| VH 3 | 0.583 | 0.410 |       |       | 0.990 | 0.696 |
| VH 4 | 0.435 | 0.291 |       |       | 0.617 | 0.486 |
| VH 5 | 1.188 | 0.757 | 0.475 | 0.525 | 1.599 | 1.206 |

TABLE 2-continued

Relative $IC_{50}$ values of all Composite Human Antibody ™ variants compared to chimeric 6B11 IgG1.

|      | VK1   | VK2   | VK3   | VK4   | VK5   | VK6   |
|------|-------|-------|-------|-------|-------|-------|
| VH 6 | 0.945 |       | 0.466 | 0.505 | 1.596 | 0.550 |
| VH 7 | 1.550 | 1.357 | 0.889 | 0.877 | 2.190 | 1.344 |
| VH 8 | 0.365 | 0.286 |       |       | 1.471 | 0.674 |

Values were calculated by dividing the $IC_{50}$ of the test antibody by that of the reference antibody and are representative of two experiments.

Eight variants with the lowest relative IC50 values were further tested in the competition ELISA to allow a more direct comparison (Table 3). This confirmed that the selected variants have improved binding profiles compared to the 6B11 chimeric reference antibody and the relative IC50 values were comparable to those from the first experiment.

TABLE 3

|          | Relative $IC_{50}$ |
|----------|--------------------|
| VH 3/VK3 | 0.342              |
| VH 2/VK4 | 0.199              |
| VH 3/VK3 | 0.354              |
| VH 3/VK4 | 0.320              |
| VH 4/VK3 | 0.282              |
| VH 4/VK4 | 0.212              |
| VH 8/VK3 | 0.293              |
| VH 8/VK4 | 0.293              |

Table 3: Relative $IC_{50}$ values of eight lead Composite Human Antibody ™ variants compared to chimeric 6B11 IgG1. Values were calculated by dividing the $IC_{50}$ of the test antibody by that of the reference antibody and are representative of two experiments.

It should be noted that while a modest improvement to binding versus control antibody might be expected in some of the variants, it was entirely unexpected to have binding improved to the extent observed. In particular, binding was improved more than 2 fold, more than 3 fold, more than 4 fold and even more than 5 fold versus control antibody.

The propensity for the Composite Human Antibody™ variants to form protein aggregates was assessed by SEC. Briefly, the four variants with the lowest relative IC50 values were selected for analysis, i.e. VH 2/Vκ4, VH 4/Vκ3, VH 4/Vκ4 and VH 8/Vκ4. 50 μl of each of variant was loaded onto Superdex™ 200 5/150 GL gel filtration column (GE Healthcare #28-9065-61) and pumped through the column using an AKTA purifier. The SEC traces were captured. The VH 2/Vκ4, VH 4/Vκ3 and VH 4/Vκ4 Composite Human Antibody™ variants showed no evidence of forming protein aggregates. However, the trace for the VH 8/Vκ4 variant appeared to show a small amount of aggregation in the 1A3 fraction.

Based on the binding data, the V region sequences of the Composite Human Antibodies™, and SEC analysis, the following antibodies were further tested: NKT T103 (6B11 chimeric IgG1 control antibody-SEQ ID Nos. 30 and 31), NKTT120 (SEQ ID Nos. 27 and 29), NKTT219 (SEQ ID Nos. 27 and 17), and NKTT320 (SEQ ID Nos. 28 and 29). NKTT120 comprises the light and heavy sequences of the VK4 light chain and VH4 light chain. NKTT219 comprises the light and heavy sequences of the VK3 and VH4. NKTT219 has the same IgG1 constant domains as NKTT120. The constant domain region of NKTT219, however, has a different glycosylation pattern compared to NKTT120 by design, because it is expressed in a cell line which has a fucosyl-transferase deletion. This results in a non-fucosylated (or afucosylated) carbohydrate pattern in the Fc portion of the molecule, which enhances its ability to bind Fc-gamma-RIII, thus enhancing its ADCC capacity (5×-10×). (See references 18-22). This has been demonstrated in in vitro binding experiments (upto 100× improvement), and in in vivo NKT cell depletion experiments in transgenic mice and monkeys (5×-10× improvement).

Example 2. Characterization of NKTT120

Measurement of binding affinity and functional characterization of NKTT120 was performed using recombinant human invariant TCR and cells, and in vivo function was tested in transgenic mice and cynomolgus monkeys. The data show that NKTT120 has high selectivity and specificity for the human invariant T cell receptor (iTCR) either in purified soluble form or as a membrane protein on iNKT cells. When bound to iTCR on cells, NKTT120 mediates the depletion of those cells. In terms of Fc-function, other studies show that NKTT120 binds to human FcγRI, C1q, and FcγRIII Finally, NKTT120-mediated iNKT cell depletion does not induce a cytokine response in in vitro human whole blood samples or in vivo in cynomolgus monkeys.

NKTT120 Binds to Hu-siTCR (Human Soluble iTCR)

Binding of NKTT120 and other anti-iNKT TCR mAbs was evaluated by ELISA and SPR, using recombinant soluble human iTCR (Hu-siTCR). In the ELISA using Hu-siTCR, NKTT120 showed an $IC_{50}$ value of 0.2 μg/ml, compared to the chimeric 6B11 mAb, with an $IC_{50}$ of 1.0 μg/ml. Subsequent analysis by SPR (BIAcore™) showed that NKTT120 has a ~60 nM $K_D$ for Hu-siTCR.

Binding of NKTT120 to Human iNKT Cells

Like the α-GalCer-loaded CD1d tetramer and mouse anti-human iTCR mAb 6B11, the humanized NKTT120 specifically binds human iNKT cells. To compare binding of the α-GalCer-loaded CD1d tetramer, 6B11 and NKTT120 to human iNKT cells, whole blood from healthy donors (purchased from Research Blood Components) was stained with each agent respectively, in conjunction with CD3 and anti-Vα24 mAbs. Clearly, NKTT120 binds as specifically to iNKT cells as do 6B11 and α-GalCer-loaded CD1d tetramer. (FIG. 1)

NKTT120 Recognizes an Overlapping Epitope on iNKT-TCR and the α-GalCer Binding Sites The NKTT120 epitope, the invariant CDR3 loop, resides in the region of the iTCR that binds to CD1d. To investigate the NKTT120 epitope, human PBMCs or a transfectant expressing the human iTCR were incubated in the presence or absence of NKTT120, followed by staining with α-Gal-Cer-loaded CD1d tetramer. The presence of NKTT120 completely abrogated tetramer binding. (FIG. 2)

Non-Reactivity with Other Human Cell Lines

To demonstrate the specificity of NKTT120 to human iNKT cells, binding of NKTT120 to in vitro-expanded human iNKT cells was compared with binding to a panel of selected human cell lines of lymphoid and non-lymphoid lineage (Table 4).

TABLE 4

| Cell Line | Lineage | NKTT120 | MHC I |
|---|---|---|---|
| Jurkat | T Lymphocyte | − | + |
| Raji | B Lymphocyte | − | + |
| THP-1 | Monocyte-macrophage | − | + |
| U937 | Promyelo-monocytic | − | + |
| K562* | Erythroleukemic | − | − |
| HEK-293 | Embryonic Kidney Epithelial | − | + |
| HeLa | Cervical Carcinoma | − | + |
| FO-1* | Melanoma | − | − |
| LNCaP | Prostate Adenocarcinoma | − | + |

A panel of human cell lines was tested for binding of NKTT120 using flow cytometry.
− no binding; + binding; *cells known not to express MHC I MHC I staining served as the positive control, while purified human IgG served as the negative control. NKTT120 did not cross-react with any of the tested cell lines, while it did bind to in vitro-expanded human iNKT cells. Seven of the nine cell lines tested recognized the anti-MHC Class I positive control mAb. As has been previously described, MHC Class I expression is absent on K562 and the FO-1 cells, so as expected, the anti-MHC Class I control mAb did not bind to these cells in the current study.

Fc-Function Analysis of NKTT120

NKTT120 is humanized IgG1 mAb and as such, it is expected to bind to human FcγRI and C1q. As part of the characterization of its IgG-Fc properties, it was evaluated in ELISA for reactivity with FcγRI and FcγRIII, and the complement component C1q. Three control antibodies were used in the characterization studies of NKTT120: (i) NKTT103, a chimeric 6B11 mAb, which shares the same IgG-Fc domains as NKTT120 but has the parental murine V domain regions; (ii) NKTT219, a humanized mAb with the same variable region as NKTT120, but which has an antibody-dependent cell-mediated toxicity (ADCC)-enhanced humanized IgG1; and NKTT320, a humanized mAb with the same variable region as NKTT120, but which has a modified IgG4 isotype. All three antibodies (NKTT120, NKTT219 and NKTT320) bind to the same iTCR epitope with similar specificities and affinities.

NKTT120 binds to FcγRI, and FcγRIII FcγRI, which is expressed on NK cells, is the primary mechanism by which therapeutic IgG1 mAbs mediate ADCC in vivo. NKTT120 also binds to C1q, which is the first subcomponent of the complement membrane attack complex, which recognizes and binds to the heavy chain of IgG, and initiates the classical complement pathway, resulting in complement-dependent cytotoxicity (CDC). The chimeric 6B11 mAb demonstrates similar Fc-binding properties as NKTT120. In subsequent BIAcore™ analysis, NKTT120 was found to bind FcγRI as well as FcγRIII, and to C1q. NKTT219, which was designed with enhanced Fc-effector function, binds to both FcγRI as well as FcγRIII, and to C1q, and thus is expected to have an improved capacity to deplete iNKT cells. In contrast, NKTT320, whose Fc-effector function was eliminated, does not recognize FcγRI, FcγRIII or C1q, and thus is not expected to cause iNKT cell depletion.

iNKT Cell Depletion in Vα24 Transgenic Mice

Mice that express the human (Vα24-Jα18) invariant TCR alpha chain transgene were used. These mice lack the murine Jα18 region, and thus are unable to produce Vα14-Jα18+ murine invariant NKT cells. All iNKT cells that are present in the mice are only able to express the transgenic human invariant TCR alpha chain and thus all carry the NKTT120 epitope. The proportion of these CD3+NK1.1+ canonical iNKT cells is very comparable to that in wild type mice (~2% of all CD3+ T cells). However, while all iNKT cells express the human invariant TCRα domain, which contains the NKTT120 epitope, due to the randomly integrated nature of the transgene, a large proportion of regular (non-iNKT) T cells express it as well. Furthermore, the human Vα24 alpha chain pairs with various endogenous mouse TCR beta chains. Some of these Vα24 alpha chain-mouse beta chain pairings seem to impair 6B11 binding, so that the majority, but not all Vα24-expressing T cells also bind 6B11 (and NKTT120). This effectively creates a "sink" for the NKTT120 and can affect the interpretation of study results. Thus, while these transgenic mice are very useful for studying the depletion of iNKT cells, they are limited as a model to study the physiological effects of NKTT120.

Taken together, in these mice the majority of CD3+ T cells (~65%) express the transgenic human Vα24 alpha chain and can be stained using a commercial anti-Vα24 mAb (C15). About 30% of CD3+ T cells bind 6B11 and NKTT120. Only 2% of CD3+ T cells co-express the NK marker NK1.1 (identifying them as canonical iNKT cells) and bind 6B11 (and NKTT120). It is important to keep in mind that in these mice, only the minority of 6B11 binding CD3+ T cells are actually iNKT cells. Still, it holds true that all iNKT cells express the human iTCR alpha chain and thus bind 6B11 and NKTT120. In the depletion experiments described below, the main focus lies on the CD3+NK1.1+ canonical iNKT cell population.

NKTT120 Rapidly, Selectively and Efficiently Depletes iNKT Cells in Vα24 Transgenic Mice To establish a dose-response for the depletion of iNKT cells by NKTT120 in peripheral blood, spleen and lymph node, Vα24 transgenic Jα18-deficient mice were dosed intraperitoneally with the indicated doses of NKTT120 (FIG. 3). Forty-eight hours after dosing, mice were sacrificed and blood, spleen and lymph node lymphocytes isolated. iNKT cell numbers were determined by flow cytometry (CD3+NK1.1+6B11+ cells). Depletion of iNKT cells was most efficient in peripheral blood, followed by spleen and lymph node. A 10-fold higher dose was needed for comparable depletion in lymph node to blood: 30 µg depleted iNKT cells in lymph node to a level that was achieved by a 3 µg dose in blood, and a similar degree of depletion in lymph node to blood was seen when comparing 100 µg and 10 µg doses, respectively.

Further, to establish a time-course of kinetics of NKTT120-mediated iNKT cell depletion, Vα24 transgenic Jα18-deficient mice were dosed intraperitoneally with 100 µg NKTT120 (n=2 per dose). At indicated time points mice were sacrificed, splenocytes isolated and iNKT cell numbers determined by flow cytometry. iNKT cell numbers were substantially reduced two hours after dosing with almost complete depletion by six hours after dosing. (FIG. 4, panel A). To further corroborate that functional iNKT cells are completely depleted by NKTT120 dosing, Vα24 transgenic Jα18-deficient mice were dosed intraperitoneally with 100 µg NKTT120. Forty-eight hours later mice were injected intravenously with 2 µg of the iNKT cell super agonist αGalCer. Two hours after this αGalCer challenge, mice were sacrificed, splenocytes harvested and analyzed for intracellular IFNγ by flow cytometry (gating on CD3+ NK1.1+ cells). The data were compared to those from control mice that had not been injected with NKTT120. While a robust IFNγ response was detected in untreated mice, pretreatment with NKTT120 abrogated any response to α-GalCer (FIG. 4, panel B).

Pharmacologic Depletion of iNKT Cells Abrogates α-GalCer-Provoked AHR

It has been demonstrated that iNKT cells that are recruited to the lung by intranasal α-GalCer challenge are sufficient to induce AHR in mice and monkeys (10, 11). In a preliminary experiment using the 6B11 chimeric antibody (NKTT103) and Vα24 transgenic mice backcrossed to the BALB/c background for six generations (BALB/c mice are generally more susceptible to Th2-inclined asthma models), it was shown that pharmacologic depletion of iNKT cells can substantially ameliorate the effect of intranasal α-GalCer challenge.

FIG. 4: Time Course of iNKT Cell Depletion by NKTT120 in Vα24 Transgenic Mice

A. Vα24 transgenic mice (n=2 per group) were injected intraperitoneally with 100 µg of NKTT120 and sacrificed at indicated time points. Gating on splenic CD3+NK1.1+ iNKT cells, the percentage of 6B11 binding cells was assessed.

B. Vα24 transgenic mice (n=2 per group) were injected with 100 µg NKTT120. A control group did not receive NKTT120. Forty-eight hours later, separate NKTT120-treated mice and control mice were injected with 2 µg α-GalCer. Two hours after α-GalCer injection, mice were sacrificed and splenic CD3+NK1.1+ iNKT cells were assayed for intracellular IFN by flow cytometry.

FIG. 5 demonstrates that pharmacological depletion of iNKT cells abrogates intra-nasally administered α-GalCer-induced AHR.

The data suggest that the mechanism of iNKT cell depletion is not via margination, but is by ADCC and/or CDC.

Preliminary Non-GLP PK/PD Study of NKTT120 in Cynomolgus Monkeys

NKTT120 was tested in two non-GLP studies using cynomolgus monkeys. In the first study, the iNKT cell depletion dose-response of NKTT120 was explored in order to define the doses at which NKTT120 depletes iNKT cells and to help guide dose selection for a more extensive PK/PD study. The cynomolgus monkey was selected for these preliminary non-GLP pharmacology and PK/PD studies because of: (i) sequence identity between the NKTT120 binding epitope (CDR3α loop of iTCR) in human and cynomolgus monkey; (ii) in vitro data that indicate positive and comparable binding of NKTT120 to cynomolgus monkey and human iNKT cells, but no significant binding of NKTT120 to iNKT cells of rodents and other species; (iii) demonstrated reactivity and specificity of NKTT120 for cynomolgus monkey iNKT cells; (iv) similarity in the iNKT cells count distribution between human and cynomolgus monkey peripheral blood.

Species Sequence Homologies to Human NKTT120 Antigen Epitope

The iTCR amino acid sequence between humans and cynomolgus monkey is similar, with the target NKTT120 binding region differing only in one amino acid (Table 5). Although the overall Vα24-J18 region is highly conserved among primate and non-primate species, the relevant NKTT120 binding epitope region in rodents and humans differs by three amino acids, which is sufficient to abrogate binding of the antibody. Thus, NKTT120 binds to iNKT cells from humans and cynomolgus and rhesus monkeys, but not to cells from squirrel monkeys or rodents. It also binds to mice that express the human Vα24-Jα18 iTCR-alpha chain transgene.

TABLE 5

| Human | CVVSDRGSTLGRLY | (SEQ ID NO: 1) |
| Cynomolgus monkey | CVVSDRGSTLG<u>K</u>LY | (SEQ ID NO: 2) |
| Rhesus monkey | CVVSDRGSTLG<u>K</u>LY | (SEQ ID NO: 2) |
| Mouse | CVV<u>G</u>DRGS<u>A</u>LGRL<u>H</u> | (SEQ ID NO: 4) |

TABLE 5-continued

| | | |
|---|---|---|
| Rat | CVV<u>A</u>DRGS<u>A</u>LG<u>K</u>LY | (SEQ ID NO: 5) |
| Pig | CVV<u>G</u>DRGS<u>R</u>LGRLY | (SEQ ID NO: 6) |

Frequencies of iNKT Cells in Human and Cynomolgus Monkey

In order to compare frequencies of iNKT cells in human and cynomolgus monkey, iNKT cell numbers in whole blood from human healthy donors (blood samples were purchased from Research Blood Components, Inc.), and cynomolgus monkey were assessed by flow cytometry. The data demonstrate comparable frequency of iNKT cells in human and cynomolgus monkey. (FIG. 6).

NKTT120 Demonstrates Similar Saturation Binding Profiles in Human and Cynomolgus Monkey iNKT Cells To measure saturation binding of NKTT120 to iNKT cells, human whole blood samples (purchased from Research Blood Components, Inc.) or cynomolgus monkey whole blood were incubated with different concentrations of NKTT120 for 30 minutes on ice and subsequently stained with fluorochrome-labeled 6B11. The titration curves show similar saturation binding (as determined by blocking of 6B11 staining) for human and cynomolgus monkey iNKT cells. Cumulatively, the data confirm that the cynomolgus monkey is the most relevant animal for the nonclinical toxicology study of NKTT120. (FIG. 7)

Dose Range-Finding iNKT Cell Depletion Study in Cynomolgus Monkey

In the dose-range finding pharmacodynamic study, six doses were tested: 0.0005, 0.001, 0.002, 0.003, 0.01 and 0.03 mg/kg (n=1 per dose). Animals were followed for seven days after dosing, during which time iNKT cells were measured by flow cytometry; data were expressed as a percent of total T cells. T and B lymphocytes, CD4+ T cells and NK cells were also monitored by flow cytometry. Clinical chemistry and hematology assessments were performed; the acute phase proteins, C-reactive protein and haptoglobin, were measured and selected cytokines GM-CSF, IL-4, IL-6, TNFα and IFNγ were measured.

NKTT120 produced a dose-dependent reduction of peripheral blood iNKT cells (FIG. 8), with complete depletion observed within 24 hours at the 0.03 mg/kg dose and lasting for the 7-day monitoring period. Partial depletion was observed at the lower doses and appeared to be reversible. No effects on iNKT cells were observed at doses of 0.003 mg/kg or lower. No overt toxicity was noted post-administration. Aside from the anticipated effect on iNKT cells, there were no other effects noted in this study that were considered test article-related.

PK/PD Study in Cynomolgus Monkeys

Based on the results of the dose range-finding study, three doses of NKTT120 (0.003, 0.03, and 0.3 mg/kg; n=3 per dose) were selected to use in a pharmacodynamic/pharmacokinetic (PK/PD) study that monitored lymphocytes for an extended period of time relative to that of the previous study (i.e., 28 days versus seven days). Flow cytometry measured iNKT cells as a percent of total T cells, and was also used to measure T and B lymphocytes, CD4+ T cells and NK cells. In addition to those parameters measured in the dose range-finding study, serum was also tested for the presence of anti-NKTT120 antibodies.

No overt toxicity was noted post-administration. The two highest doses completely depleted iNKT cells for the duration of the study, while the low dose reduced iNKT cells to about 50% of baseline and returned to ~80% of baseline by day four (FIG. 9). No other test article-related changes in T and B cells were noted (FIG. 10). No anti-NKTT120 antibodies were detected.

Although the dose range-finding study showed that iNKT cells are depleted rapidly, and that serum cytokine levels did not increase as a result, a theoretical possibility exists that cytokines could be released as a result of NKTT120 binding to iNKT cells, prior to their depletion, so selected cytokines (GM-CSF, IL-4, IL-6, TNFα and IFNγ) were measured to confirm the prior result. There were no effects on cytokines.

Overall, the conclusions is that NKTT120 administration results in the specific depletion of peripheral iNKT cells in a reversible and dose-dependent manner, in the absence of significant effects upon other hematological, biochemical or immunological parameters.

Pharmacokinetic Analysis of NKTT120 in Cynomolgus Monkeys

The PK of NKTT120 was evaluated. The PK analysis showed that NKTT120 possesses a consistent PK profile across all doses, with parameters that are fairly typical of monoclonal antibody therapeutics, including a half-life of about 11 days. Pharmacokinetic parameters for NKTT120 administered to cynomolgus monkeys following a single intravenous dose are shown in Table 6 and Table 7.

TABLE 6

Pharmacokinetic Parameters for NKTT120 in Cynomolgus Monkeys

| Dose (mg/kg) | $AUC_{0-\infty}$ (hr·ng/mL) | $AUC_{0-\infty}$/dose [(hr·ng/mL)/mg/kg] | $AUC_{0-672}$ (hr·ng/mL) | $AUC_{0-672}$/dose [(hr·ng/mL)/mg/kg] |
|---|---|---|---|---|
| 0.003 | 10500 ± 2380 | 3510000 ± 794000 | 8320 ± 1250 | 2770000 ± 416000 |
| 0.03 | 148000 ± 23600 | 4950000 ± 787000 | 124000 ± 17500 | 4130000 ± 583000 |
| 0.3 | 1620000 ± 182000 | 5410000 ± 608000 | 1370000 ± 123000 | 4580000 ± 411000 |

TABLE 7

Pharmacokinetic Parameters for NKTT120 in Cynomolgus Monkeys

| Dose (mg/kg) | Cl (mL/min/kg) | $t_{1/2}$ (hr) | $V_{SS}$ (mL/kg) |
|---|---|---|---|
| 0.003 | 0.00493 ± 0.00118 | 306 ± 61.2 | 117 ± 0.494 |
| 0.03 | 0.00342 ± 0.0005000 | 263 ± 43.5 | 75.91 ± 13.1 |
| 0.3 | 0.00311 ± 0.000329 | 253 ± 26.6 | 64.8 ± 6/09 |

PK/PD Study in Cynomolgus Monkeys with iNKT Cell Antibody Possessing ADCC-Enhanced IgG-Fc Effector Function The effect of NKTT120 on iNKT cell depletion was compared to an antibody with ADCC-enhanced IgG-Fc effector function (NKTT219), but the same antigen specificity and affinity. NKTT120 and NKTT219 were administered intravenously to cynomolgus monkeys at 0.003 mg/kg, each and iNKT cells were measured at time points over 28 days. The data establish complete depletion of iNKT cells at a 0.003 mg/kg dose of NKTT219, compared to a partial depletion mediated by NKTT120 at the same dose. These data confirm that the iNKT cell depletion is mediated by ADCC, as a 10-fold enhanced activity was expected, and observed, with NKTT219 in this study. The data also corroborate the concept that the transient decrease in iNKT cells observed at the low dose of 0.003 mg/kg of NKTT120 is due to partial depletion, as complete depletion is achieved with the same dose of NKTT219, which possesses enhanced ADCC activity.

As a negative control for the depleting mAbs (NKTT120 and NKTT219), NKTT320, which lacks Fc-effector functions, was tested at doses up to 30-fold higher than that of NKTT120 and did not deplete iNKT cells. The data from both control antibodies (the enhanced depleting antibody, NKTT219, and the non-depleting antibody, NKTT320) confirm that NKTT120 does deplete iNKT cells, as opposed to masking the iTCR epitope or sequestering the iNKT cells.

NKTT120 does not Induce a Cytokine Response in Human Whole Blood In Vitro

To address the possibility of cytokine release in response to treatment with NKTT120 in humans, we evaluated the effect of NKTT120 in a human whole blood experiment. After measuring iNKT cell numbers by flow cytometry, whole blood was incubated in TruCulture™ tubes for 24 hours in the presence or absence of 20 µg/ml (this concentration is higher than the predicted plasma exposure following a dose of 1 mg/kg) of NKTT120. As a positive control, whole blood was incubated in anti-CD3 mAb-containing tubes. After 24 hours, supernatant was collected, frozen and shipped to Rules-Based Medicine (TX) for multiplex cytokine analysis. The analytes tested are listed in Table 8.

TABLE 8

| | |
|---|---|
| Alpha-1-Antitrypsin (AAT) | Interleukin-1 receptor antagonist (IL-1ra) |
| Beta-2-Microglobulin (B2M) | Interleukin-2 (IL-2) |
| Brain-Derived Neurotrophic Factor (BDNF) | Interleukin-23 (IL-23) |
| Complement C3 (C3) | Interleukin-3 (IL-3) |
| C-Reactive Protein (CRP) | Interleukin-4 (IL-4) |
| Eotaxin-1 | Interleukin-5 (IL-5) |
| Factor VII | Interleukin-6 (IL-6) |
| Fibrinogen | Interleukin-7 (IL-7) |
| Ferritin (FRTN) | Interleukin-8 (IL-8) |
| GM-CSF | Monocyte Chemotactic Protein 1 (MCP-1) |
| Haptoglobin | Macrophage Inflammatory Protein-1 alpha (MIP-1 alpha) |
| Intercellular Adhesion Molecule 1 (ICAM-1) | Macrophage Inflammatory Protein-1 beta (MIP-1 beta) |
| Interferon gamma (IFN-gamma) | Matrix Metalloproteinase-2 (MMP-2) |
| Interleukin-1 alpha (IL-1 alpha) | Matrix Metalloproteinase-3 (MMP-3) |
| Interleukin-1 beta (IL-1 beta) | Matrix Metalloproteinase-9 (MMP-9) |
| Interleukin-10 (IL-10) | T Cell-Specific Protein RANTES (RANTES) |
| Interleukin-12 Subunit p40 (IL-12p40) | Stem Cell Factor (SCF) |
| Interleukin-12 Subunit p70 (IL-12p70) | Tissue Inhibitor of Metalloproteinases 1 (TIMP-1) |
| Interleukin-15 (IL-15) | Tumor Necrosis Factor alpha (TNF-alpha) |
| Interleukin-17 (IL-17) | Tumor Necrosis Factor beta (TNF-beta) |
| Interleukin-18 (IL-18) | Tumor Necrosis Factor Receptor 2 (TNFR2) |

TABLE 8-continued

| | |
|---|---|
| Vascular Endothelial Growth Factor (VEGF) | Vascular Cell Adhesion Molecule-1 (VCAM-1) |
| von Willebrand Factor (vWF) | Vitamin D-Binding Protein (VDBP) |

The results of multiplex cytokine analysis are shown in FIG. 11 (only data for cytokines that showed a change from untreated control levels are shown). Substantial elevation of several cytokines (IFNγ, IL-4, IL-10, IL-17, TNF-α, IL-2, IL-5, IL-8, IL-1 RA and MIP-1β) was induced by the anti-CD3 positive control in at least two of four tested donors. However, NKTT120 did not induce any cytokine response in any of the four donor samples. The data demonstrate that NKTT120-mediated iNKT cell depletion has no measurable cytokine-inducing effect in an in vitro human whole blood setting.

Demonstration of iNKT Cell Activation by Humanized Anti-iNKT mAbs Designed with Reduced Fc-Effector Function NKTT320 is a humanized mAb which specifically recognizes human iTCR. It is a modified IgG4 mAb with two amino acid changes introduced in the hinge region, one designed to stabilize the IgG4 heavy chain dimer formation, and the $2^{nd}$ to reduce residual FcγR binding capacity (Newman et al., Clin Immunol 98, 164-174). The study below demonstrates that NKTT320 can activate human iNKT cells in human whole blood from healthy donors.

Human whole blood was diluted in RPMI and incubated with 20 µg/ml control IgG or 20 µg/ml NKTT320 overnight at 37° C., 5% CO2. Samples were then surface stained with anti CD3, CD4, Va24, Vb11, CD25 and CD69. RBC were lysed, and cells were fixed, permeabilized and stained for intracellular IFN-γ and IL-4, and flow cytometry analysis conducted on a BD LSR Fortessa. iNKT cells were identified by CD3, Va24 and Vb11 staining.

The results show that NKTT320 induces expression of intracellular IFN-γ and IL-4 in human whole blood from healthy volunteers (FIG. 12). Upregulation of the activation marker CD69 and CD25 was also observed (data not shown).

REFERENCES

1. Van Kaer, L. 2007. NKT cells: T lymphocytes with innate effector functions. *Curr Opin Immunol* 19:354-364.
2. Van Kaer, L., V. V. Parekh, and L. Wu. 2010. Invariant natural killer T cells: bridging innate and adaptive immunity. *Cell Tissue Res* 343:43-55.
3. Umetsu, D. T., and R. H. Dekruyff. 2010. Natural killer T cells are important in the pathogenesis of asthma: the many pathways to asthma. *J Allergy Clin Immunol* 125: 975-979.
4. Bendelac, A., P. B. Savage, and L. Teyton. 2007. The biology of NKT cells. *Annu Rev Immunol* 25:297-336.
5. Matsuda, J. L., T. Mallevaey, J. Scott-Browne, and L. Gapin. 2008. CD1d-restricted iNKT cells, the 'Swiss-Army knife' of the immune system. *Curr Opin Immunol* 20:358-368.
6. Wu, L., and L. Van Kaer. 2009. Natural killer T cells and autoimmune disease. *Curr Mol Med* 9:4-14.
7. Lisbonne, M., S. Diem, A. de Castro Keller, J. Lefort, L. M. Araujo, P. Hachem, J. M. Fourneau, S. Sidobre, M. Kronenberg, M. Taniguchi, P. Van Endert, M. Dy, P. Askenase, M. Russo, B. B. Vargaftig, A. Herbelin, and M. C. Leite-de-Moraes. 2003. Cutting edge: invariant V alpha 14 NKT cells are required for allergen-induced 8. Lombardi, V., P. Stock, A. K. Singh, J. Kerzerho, W. Yang, B. A. Sullivan, X. Li, T. Shiratsuchi, N. E. Hnatiuk, A. R. Howell, K. O. Yu, S. A. Porcelli, M. Tsuji, M. Kronenberg, S. B. Wilson, and O. Akbari. 2010. A CD1d-dependent antagonist inhibits the activation of invariant NKT cells and prevents development of allergen-induced airway hyperreactivity. *J Immunol* 184:2107-2115.
9. Pichavant, M., S. Goya, E. H. Meyer, R. A. Johnston, H. Y. Kim, P. Matangkasombut, M. Zhu, Y. Iwakura, P. B. Savage, R. H. DeKruyff, S. A. Shore, and D. T. Umetsu. 2008. Ozone exposure in a mouse model induces airway hyperreactivity that requires the presence of natural killer T cells and IL-17. *J Exp Med* 205:385-393.
10. Matangkasombut, P., M. Pichavant, T. Yasumi, C. Hendricks, P. B. Savage, R. H. Dekruyff, and D. T. Umetsu. 2008. Direct activation of natural killer T cells induces airway hyperreactivity in nonhuman primates. *J Allergy Clin Immunol* 121:1287-1289.
11. Meyer, E. H., S. Goya, O. Akbari, G. J. Berry, P. B. Savage, M. Kronenberg, T. Nakayama, R. H. DeKruyff, and D. T. Umetsu. 2006. Glycolipid activation of invariant T cell receptor+ NK T cells is sufficient to induce airway hyperreactivity independent of conventional CD4+ T cells. *Proc Natl Acad Sci USA* 103:2782-2787.
12. Kim, E. Y., J. T. Battaile, A. C. Patel, Y. You, E. Agapov, M. H. Grayson, L. A. Benoit, D. E. Byers, Y. Alevy, J. Tucker, S. Swanson, R. Tidwell, J. W. Tyner, J. D. Morton, M. Castro, D. Polineni, G. A. Patterson, R. A. Schwendener, J. D. Allard, G. Peltz, and M. J. Holtzman. 2008. Persistent activation of an innate immune response translates respiratory viral infection into chronic lung disease. *Nat Med* 14:633-640.
13. Matangkasombut, P., G. Marigowda, A. Ervine, L. Idris, M. Pichavant, H. Y. Kim, T. Yasumi, S. B. Wilson, R. H. DeKruyff, J. L. Faul, E. Israel, O. Akbari, and D. T. Umetsu. 2009. Natural killer T cells in the lungs of patients with asthma. *J Allergy Clin Immunol* 123:1181-1185.
14. Reynolds, C., J. Barkans, P. Clark, H. Kariyawasam, D. Altmann, B. Kay, and R. Boyton. 2009. Natural killer T cells in bronchial biopsies from human allergen challenge model of allergic asthma. *J Allergy Clin Immunol* 124: 860-862; author reply 862.
15. Exley, M. A., R. Hou, A. Shaulov, E. Tonti, P. Dellabona, G. Casorati, O. Akbari, H. O. Akman, E. A. Greenfield, J. E. Gumperz, J. E. Boyson, S. P. Balk, and S. B. Wilson. 2008. Selective activation, expansion, and monitoring of human iNKT cells with a monoclonal antibody specific for the TCR alpha-chain CDR3 loop. *Eur J Immunol* 38:1756-1766.
16. Kuns, R. D., E. S. Morris, K. P. Macdonald, K. A. Markey, H. M. Morris, N. C. Raffelt, T. Banovic, A. L. Don, V. Rowe, A. C. Burman, A. D. Clouston, C. Farah, G. S. Besra, P. A. Illarionov, M. J. Smyth, S. A. Porcelli, and G. R. Hill. 2009. Invariant natural killer T cell-natural killer cell interactions dictate transplantation outcome after alpha-galactosylceramide administration. *Blood* 113: 5999-6010.
17. Lehuen, A., J. Diana, P. Zaccone, and A. Cooke. Immune cell crosstalk in type 1 diabetes. *Nat Rev Immunol* 10:501-513.
18. Shinkawa, T., K. Nakamura, N. Yamane, E. Shoji-Hosaka, Y. Kanda, M. Sakurada, K. Uchida, H. Anazawa, M. Satoh, M. Yamasaki, N. Hanai, and K. Shitara. 2003. The absence of fucose but not the presence of galactose or bisecting N-acetylglucosamine of human IgG1 complex-type oligosaccharides shows the critical role of enhancing antibody-dependent cellular cytotoxicity. *J Biol Chem* 278:3466-3473.
19. Niwa, R., E. Shoji-Hosaka, M. Sakurada, T. Shinkawa, K. Uchida, K. Nakamura, K. Matsushima, R. Ueda, N. Hanai, and K. Shitara. 2004. Defucosylated chimeric anti-CC chemokine receptor 4 IgG1 with enhanced antibody-dependent cellular cytotoxicity shows potent therapeutic activity to T-cell leukemia and lymphoma. *Cancer Res* 64:2127-2133.
20. Tojo, S., A. Okazaki, M. Wakitani, T. Shinkawa, K. Uchida, and T. Suzawa. 2009. A chromatographic approach for elevating the antibody-dependent cellular cytotoxicity of antibody composites. *Biol Pharm Bull* 32:1604-1608.
21. Busse, W. W., R. Katial, D. Gossage, S. Sari, B. Wang, R. Kolbeck, A. J. Coyle, M. Koike, G. L. Spitalny, P. A. Kiener, G. P. Geba, and N. A. Molfino. 2010. Safety profile, pharmacokinetics, and biologic activity of MEDI-563, an anti-IL-5 receptor alpha antibody, in a phase I study of subjects with mild asthma. *J Allergy Clin Immunol* 125:1237-1244 e1232.
22. Junttila, T. T., K. Parsons, C. Olsson, Y. Lu, Y. Xin, J. Theriault, L. Crocker, O. Pabonan, T. Baginski, G. Meng, K. Totpal, R. F. Kelley, and M. X. Sliwkowski. 2010. Superior in vivo efficacy of afucosylated trastuzumab in the treatment of HER2-amplified breast cancer. *Cancer Res* 70:4481-4489.

---

We claim:

1. A method of treatment to suppress an immune response, comprising administering to a subject in need of treatment a naked blocking antibody that binds selectively to iNKT cells in an amount that is effective to suppress the subject's iNKT cell function, wherein the subject has an airway hyper-reactivity condition or sickle cell anemia, and wherein the antibody comprises a heavy chain with a sequence that is SEQ ID No. 27 and a light chain with a sequence that is SEQ ID No. 29.

2. The method of claim 1, wherein the subject has an airway hyper-reactivity condition and the airway hyper-reactivity condition is asthma.

3. The method of claim 2, wherein the asthma is allergic asthma.

4. The method of claim 1, wherein the subject has an airway hyper-reactivity condition and the airway hyper-reactivity condition is COPD.

5. The method of claim 1, wherein the subject has an airway hyper-reactivity condition and the treatment suppresses in the subject one or more symptoms of the condition.

6. The method of claim 1, wherein the subject is human.

7. The method of claim 1, wherein the subject has sickle cell anemia.

* * * * *